United States Patent
Kerschen et al.

(10) Patent No.: US 9,458,188 B2
(45) Date of Patent: Oct. 4, 2016

(54) EFFICIENT PEPTIDE COUPLINGS AND THEIR USE IN THE SYNTHESIS AND ISOLATION OF A CYCLOPENTA (G) QUINAZOLINE TRISODIUM SALT

(75) Inventors: James Alan Kerschen, Somerset, NJ (US); Alexander James Bridges, Saline, MI (US); Milind D. Choubal, Mundelein, IL (US); Sean Mark Dalziel, San Francisco, CA (US); Thomas Elliott Jacks, Hillsborough, NJ (US); Andrew S. Thompson, Mountainside, NJ (US); James Robert Zeller, Scottsdale, AZ (US)

(73) Assignee: BTG INTERNATIONAL LIMITED, London (GB)

( * ) Notice: Subject to any disclaimer, the term of this patent is extended or adjusted under 35 U.S.C. 154(b) by 130 days.

(21) Appl. No.: 13/996,618

(22) PCT Filed: Dec. 19, 2011

(86) PCT No.: PCT/US2011/065752
§ 371 (c)(1),
(2), (4) Date: Sep. 10, 2013

(87) PCT Pub. No.: WO2012/087888
PCT Pub. Date: Jun. 28, 2012

(65) Prior Publication Data
US 2013/0345423 A1    Dec. 26, 2013

Related U.S. Application Data

(60) Provisional application No. 61/459,952, filed on Dec. 22, 2010.

(51) Int. Cl.
*C07F 7/02* (2006.01)
*C07K 1/08* (2006.01)
*C07F 7/18* (2006.01)
*C07K 5/02* (2006.01)
*C07C 271/20* (2006.01)
*C07D 403/12* (2006.01)
*C07F 7/10* (2006.01)
*C07K 1/10* (2006.01)
*C07K 1/16* (2006.01)
*C07K 1/36* (2006.01)
*C07D 239/90* (2006.01)

(52) U.S. Cl.
CPC ............. *C07K 1/088* (2013.01); *C07C 271/20* (2013.01); *C07D 239/90* (2013.01); *C07D 403/12* (2013.01); *C07F 7/10* (2013.01); *C07F 7/1896* (2013.01); *C07K 1/10* (2013.01); *C07K 1/16* (2013.01); *C07K 1/36* (2013.01); *C07K 5/0215* (2013.01)

(58) Field of Classification Search
CPC ....................................................... C07F 7/02
See application file for complete search history.

(56) References Cited

PUBLICATIONS

Alexander, J.P., et al. "γ-Glutamyl Hydrolase: Kinetic Characterization of Isopeptide Hydrolysis Using Fluorgenic Substrates." Biochemistry. (2008), vol. 47, pp. 1228-1239.*
American Chemical Society. STN Database. RN 6893-26-1.*
American Chemical Society. STN Database. RN 6931-86-8.*

* cited by examiner

*Primary Examiner* — Noble Jarrell
*Assistant Examiner* — John S Kenyon
(74) *Attorney, Agent, or Firm* — Tarolli, Sundheim, Covell & Tummino LLP

(57) ABSTRACT

A new method for the synthesis of L-Glutamyl-γ-D-Glutamic acid and its use in the synthesis of (2R)-((4S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino) benzamido)butanamido)pentanedioic acid, 1 are provided. Also provided is an efficient method for the isolation and purification of the trisodium salt of the abovementioned acid, 2, in a form suitable for long term storage and use in a parenteral dosing form.

20 Claims, No Drawings

US 9,458,188 B2

EFFICIENT PEPTIDE COUPLINGS AND THEIR USE IN THE SYNTHESIS AND ISOLATION OF A CYCLOPENTA (G) QUINAZOLINE TRISODIUM SALT

CROSS-REFERENCE TO RELATED APPLICATIONS

This application is the U.S. national phase entry of PCT/US2011/065752, with an international filing date of Dec. 19, 2011, which claims priority from U.S. Provisional Application Ser. No. 61/459,952, filed Dec. 22, 2010, the entire contents of which are incorporated herein by reference.

TECHNICAL FIELD

The present invention relates to the synthesis of (R)-2-((S)-4-amino-4-carboxybutanamido)pentanedioic acid (L-Glutamyl-γ-D-Glutamic acid, L-Glu-γ-D-Glu) and its use in synthesis, in particular in the synthesis of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)-pentanedioic acid, and to the isolation and purification of the aforementioned acid as its trisodium salt.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where methods or processes are expressed herein as lists or sequences of steps, including as lists of numbered, lettered, or bulleted steps, the order in which these steps is presented is not intended to imply any particular order or timing of the steps in the method, unless a particular order is required or is explicitly stated. Unless otherwise provided, therefore, the steps of each disclosed method can be carried out in any sensible order, as is clear to one skilled in the art i.e. any order which is suitable to achieve the stated purpose or product of that method. Also, unless expressly stated, the presence of additional steps in the methods is not excluded.

The novel thymidilate synthase inhibitor (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid 1, as its trisodium salt 2 (also known as CB300945, BCG945, or ONX-0801) is a very potent inhibitor of thymidilate synthase, with an $IC_{50}$ of 3 nM for the enzyme.

Unlike most thymidilate synthase inhibitors such as Methotrexate, and Pemetrexed, 2 does not require polyglutamoylation for its activation, or for cellular retention, and it is not a substrate for the polyglutamoylation synthase enzyme.

Furthermore, 2 is not a substrate for the commonly expressed reduced folate carrier protein (RFCP) with a $K_i$>250 μM, and does not pass readily through regular cell membranes. However, it does bind to the folate receptor α (FRα) with a very high, subnanomolar affinity ($K_i$ 0.5 nM), and can be transported into cells at a modest rate via that receptor, even when serum levels of 2 are very low.

Once in the cells, 2 inhibits thymidilate synthase and, as it is degraded and expelled from cells slowly, it produces a long lasting inhibition of thymidilate synthase. This results in DNA processing errors, which initiate a repair cycle, which is ultimately futile due to the lack of thymidine triphosphate for incorporation into the DNA. This leads to apoptotic DNA damaging responses and cell death.

This is the general mode of action of thymidilate synthase inhibitors, and clinical experience shows that they have a strong cytotoxic effect in human tumors, but their use is hampered by their rather broad spectrum toxicity, where target tissues, especially bone marrow, are seriously affected by the cytotoxicity of the drugs.

The current generation of thymidilate synthase inhibitors, being good substrates for the ubiquitously expressed RFCP, are distributed well into most tissues, whereas 2 is only distributed efficiently into tissues which express, or preferably overexpress, FRα. Relatively few tissues endogenously express FRα, even at modest levels. Most tissues that do express it do so in a polarized fashion on the distal face of cells, meaning that there are no transporters on the side of the cell facing the circulatory endothelium. This has the consequence that even in these tissues, penetration of 2 tends to be very inefficient. This means that high circulating levels of 2 in the plasma lead to rather low systemic toxicities.

If the same were true of tumors, it would also be expected to lead to low anti-tumor efficacy. However, there are certain classes of tumor tissues which tend to overexpress FRα. Being tumor cells, they have lost their polarity and express FRα on both apical and distal faces. Thus, these tumor tissues have the unusual propensity of being able to concentrate quite large, cytotoxic, doses of 2 in their cells from plasma drug levels low enough to have very little toxic effect. This leads to an enhanced therapeutic index for 2 in the overexpressing tumor types.

There are several tumor types which overexpress FRα, the most notable of which is ovarian cancer, where 90% of the commonest tumor type, the mucinous form of the cancer, overexpress FRα. Thus 2 is a very attractive chemotherapeutic agent for the treatment of FRα-overexpressing cancers, especially ovarian cancer, although it is not limited to that one tumor type, with uterine cancer, mesothelioma and kidney cancer, amongst others, having high percentages of FRα overexpression.

Compounds 1 and 2, along with several close congeners, are disclosed in WO2003/020748, albeit as a 1:1 mixture of diastereoisomers at the 6-position.

Scheme 1. Original Synthesis of Compound 1 as a pair of 6-Diastereoisomers

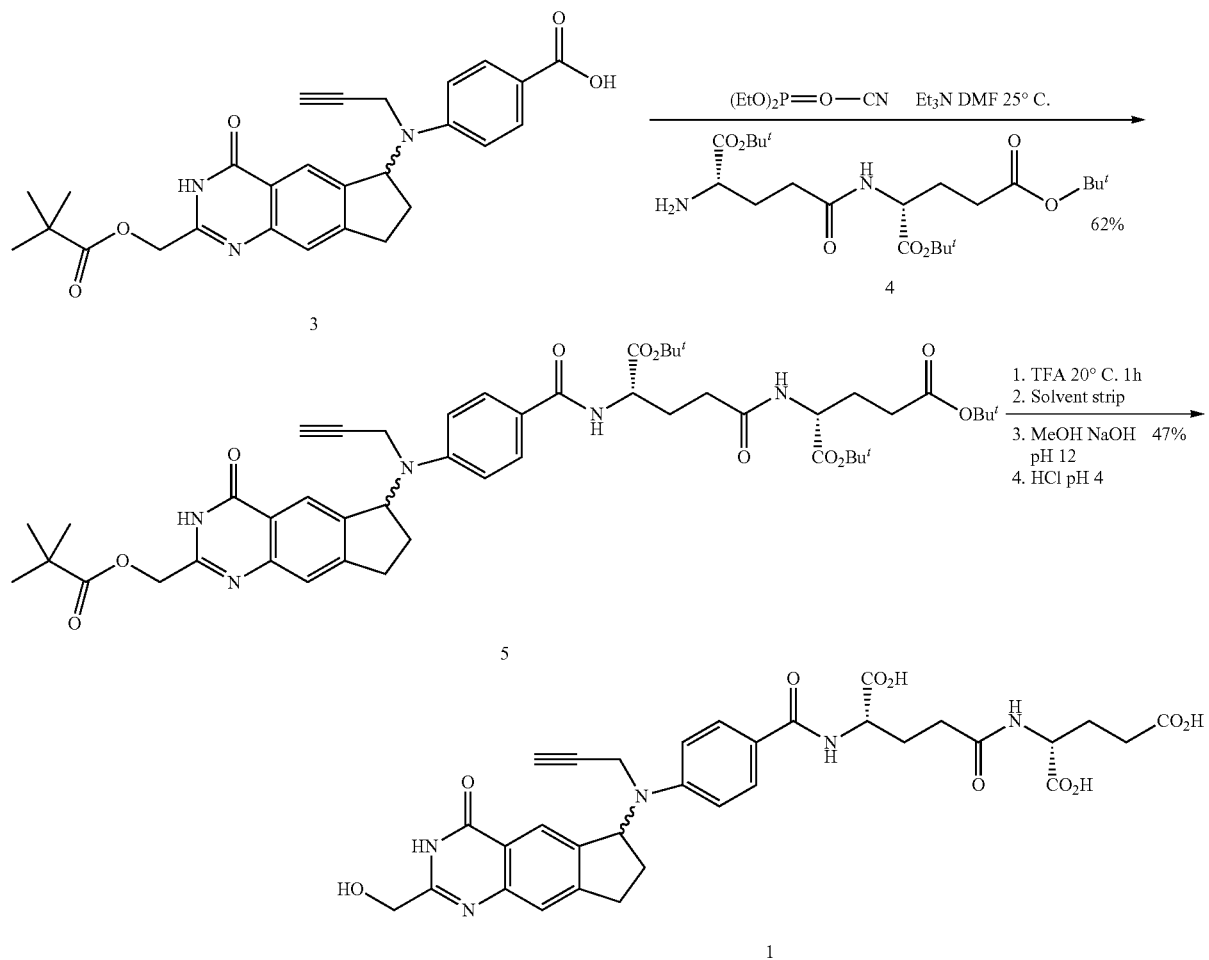

WO 2003/020748 also reveals how to synthesize compound 1, once again as a mixture of diastereoisomers at the 6-position.

As shown in Scheme 1, the cyclopentaquinazolinylaminobenzoic acid 3 is condensed with tri-O-t-butyl L-glutamyl-γ-D-glutamate, 4, using diethylphosphononitrile and triethylamine in DMF at room temperature to give tri-O-t-butyl N-{N-{4-[N-((6RS)-2-(2,2-dimethylpropionyloxymethyl)-4-oxo-3,4,7,8-tetrahydro-3H-cyclopenta[g]quinazolin-6-yl)-N-(prop-2-ynyl)amino]benzoyl}-L-γ-glutamyl}-D-glutamate 5, in 62% yield, on a low milligram scale. The three t-butyl esters are then removed by treatment with TFA at room temperature for 1 hour, the solvent is stripped at room temperature or below, and a solvent exchange is carried out to 1:1 methanol:water. The pH is raised to 12 with sodium hydroxide solution, and the pivaloyl ester hydrolyzed at room temperature. The solution is then acidified to pH 4 with 1M hydrochloric acid and precipitated at 0° C. to give acid 1 (6RS mixture) in 47% yield after filtration and drying.

Scheme 2. Synthesis of N-Methyl Analogue of Acid 1 from Hydroxyacid 7.

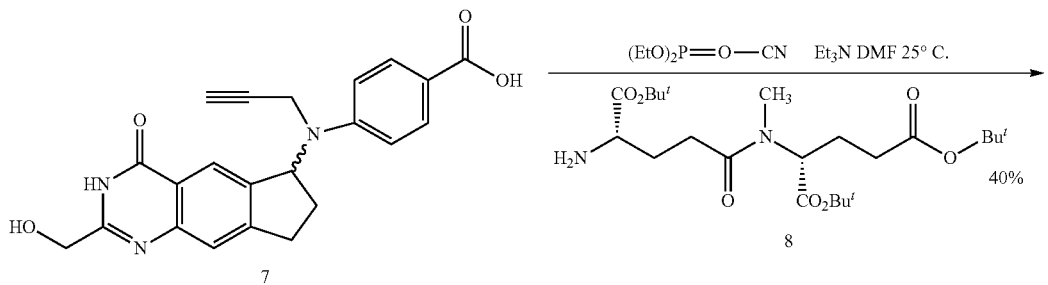

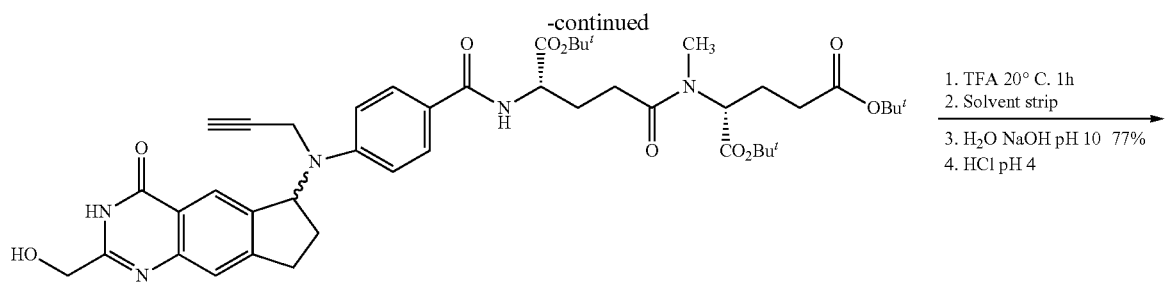

9

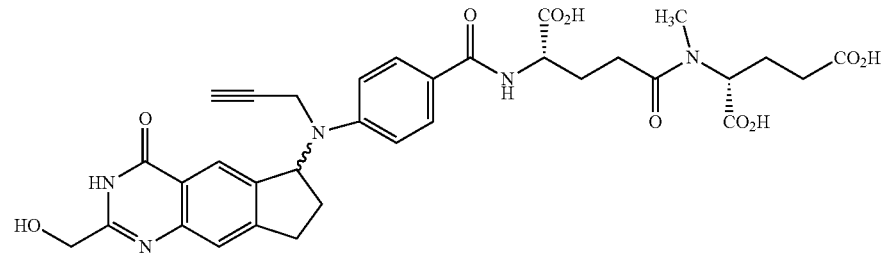

6

In U.S. Pat. No. 7,250,511 the same synthesis is disclosed for Compound 1, but a more useful variant is revealed for compound 6, as shown in Scheme 2. Compound 6 is simply compound 1, N-methylated on the D-Glu amine. In this case, depivaloylated core acid 7 is coupled with 8, the N-methylated analogue of dipeptide tri-ester 4, under the same conditions as described for the coupling of 3 and 4, to give the protected compound 9 in 40% yield. The three t-butyl esters are then removed by treatment with TEA at room temperature for 1 hour, and the solvent was then stripped at room temperature or below, and the residue was taken up in water, basified to pH 10 with dilute sodium hydroxide, and the final acid was precipitated with 1M hydrochloric acid, filtered and dried as previously to give acid 6 (6RS mixture) in 77% yield.

A method of resolving compounds of general formula (I) is revealed in WO 94/11354, in order to get the more active, and hence more desired, (6S)-enantiomers. This method involves taking racemic acids of formula (I) and condensing them with a chiral amino acid, preferably L-glutamic acid, or (S)-2-aminoadipic acid to form an amide of formula (II) as a 1:1 mixture of diastereoisomers.

Use of an appropriate protease, such as Carboxypeptidase $G_2$ selectively hydrolyzes the 6R-diastereoisomer, allowing for a straightforward separation of 6S-(II) from 6R-(1). The 6S-(II) is then hydrolyzed enzymatically to 6S-(I) in >98% enantiomeric excess. It is assumed that this process was carried out on acid 3, or possibly acid 7, since U.S. Pat. No. 7,528,141 reveals biological data on the pure 6S diastereoisomer of compound 1, but does not disclose how this isomer was made.

Tri-O-t-butyl L-glutamyl-γ-D-glutamate, 4 can be purchased commercially as its N-benzyloxycarbonyl-protected precursor 10, which is stable, and it is conveniently deblocked to free amine 4 by catalytic hydrogenation shortly prior to use. However, although the two starting materials for dipeptide 4, N-Cbz-L-Glu, 11 and D-Glu 12 are not very expensive, the two t-butyl esters N-Cbz-Glu-α-O-t-Bu 13, obtained in only 33% yield from 11 in the one step preparation, and di-O-t-butyl-D-glutamate 14, are expensive, with the result that compound 10, as produced in Scheme 3, is very expensive.

Scheme 3. Shortest synthesis of tri-O-t-butyl L-glutamyl-γ-D-glutamate, 4.

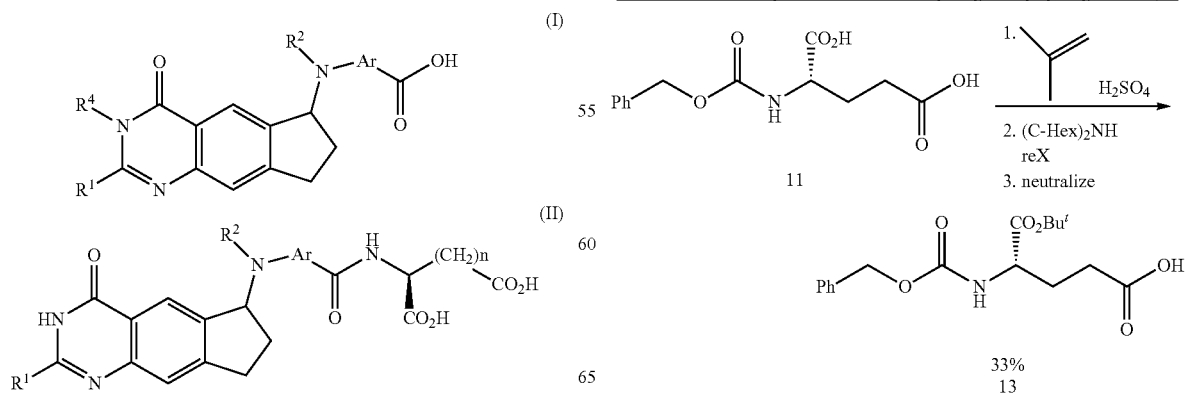

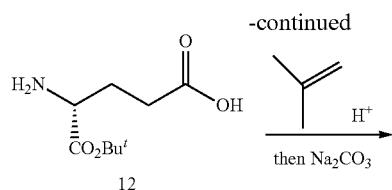

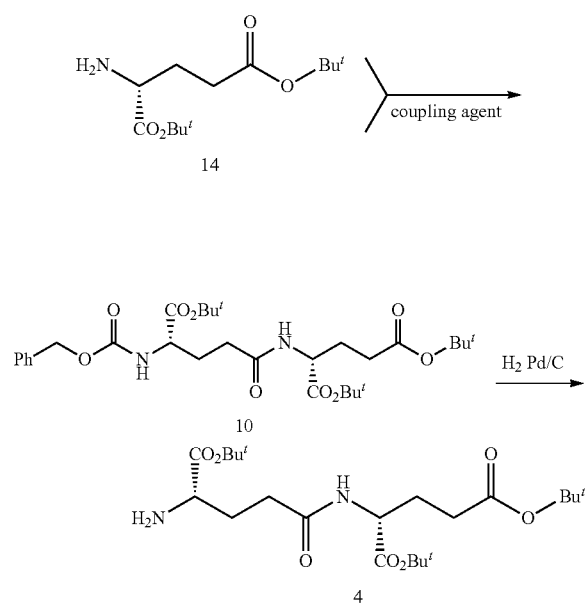

Although there are higher yielding preparations of 13, they are multistep processes, which do not reduce the cost of the compound. Therefore, dipeptide 10 is very expensive, even on large scales. Thus, an improved synthesis of 10, or use of a less expensive form of the (R)-2-((S)-4-amino-4-carboxybutanamido)pentanedioic acid dipeptide, (hereafter referred to as either L-Glu-γ-D-Glu or L-Glutamyl-γ-D-Glutamic acid) in the coupling reaction, could have very beneficial effects on the production costs for compound 1.

As set out above, the prior art methods for addition of the dipeptide unit of compound 1 to the heterocyclic core (i.e. molecules 3 and 7) involve a coupling step and one or two deprotecting steps before isolation of the final product. This chemistry has several flaws, in addition to its high cost, which make it very poorly suited to commercially manufacturing a drug.

The reported chemistry was carried out on a very small scale, with no detailed analysis of the purity profile of the product 1. Examination of compound 1 under acidic conditions, with appropriate analytical techniques not previously described for compound 1, reveals it to have limited stability below pH 5 in aqueous solution. It has also been found that the simple monotrifluoroacetate salt of 1 has limited stability, both in the solid form and in trifluoroacetic acid (TFA) solution.

As removal of the t-butyl esters from 5, or its 2-depivaloylated equivalent, require strongly acidic conditions, this is very constraining on the actual set-up required for the deprotection. Trifluoroacetic acid can be stripped from the reaction mixture. However, the stability problems of 1 in TFA solution require that, as the scale is increased, the removal of the trifluoroacetic acid must be done at low temperature and relatively quickly. Without very specialized apparatus, this cannot easily be scaled up to any great extent. It is suggested that this chemistry would become totally impractical when producing API (Active Pharmaceutical Ingredient) in the 0.5 to 1 kg scale.

Furthermore, as this compound is used parenterally, the insoluble free acid 1 cannot be the drug product, and the above-referenced patent applications do not teach an efficient preparation and adequate purification of the sodium salt 2, which is the form in the final drug product. Due of the potent anti-cancer activity of 2, superior methods of synthesis of 2 have great value and utility.

SUMMARY OF THE INVENTION

The present invention provides a new method for the synthesis of a L-Glutamyl-γ-D-Glutamic acid dipeptide, and its use in the synthesis of (2R)-((4S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, 1. Advantageously, the method of the invention may allow synthesis of a L-Glutamyl-γ-D-Glutamic acid dipeptide, preferably the unprotected L-Glutamyl-γ-D-Glutamic acid dipeptide, from readily available and cheap precursors. Also provided is an efficient method for the isolation and purification of 2 the trisodium salt of the abovementioned acid, in a form suitable for long term storage and use in a parenteral dosing form.

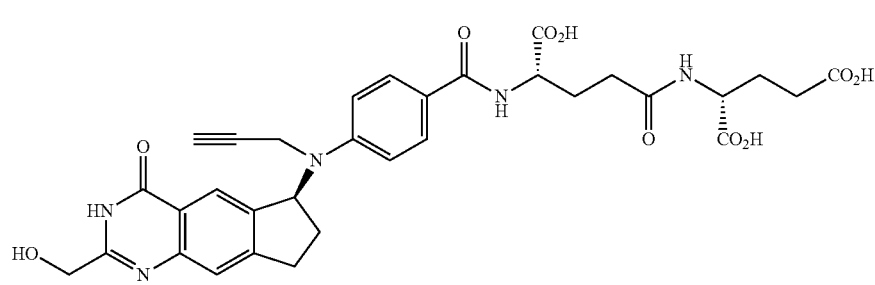

-continued

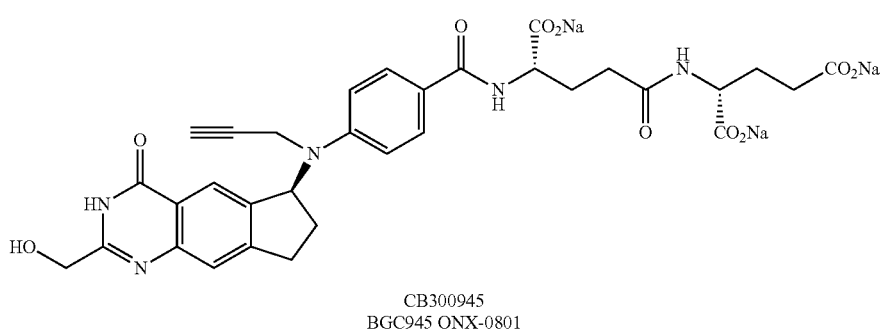

CB300945
BGC945 ONX-0801

In a first aspect, the present invention provides a method for the synthesis of a L-Glu-γ-D-Glu comprising the steps of:

a) activating the γ-carboxylic acid of an N-αO-diprotected L-Glu derivative;

b) silylating D-glutamic acid; and c) reacting the activated carboxylic acid derivative produced in step a) with the silylated product of step b) to give a protected L-Glu-γ-D-Glu species.

In some embodiments, the method further comprises:

d) deprotecting said protected L-Glu-γ-D-Glu species.

In a second aspect, the invention provides a method for the synthesis of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)-pentanedioic acid, or a pharmaceutically acceptable salt or solvate thereof, comprising the step of coupling a protected L-Glu-γ-D-Glu species with (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid.

Preferably, said protected L-Glu-γ-D-Glu species is a L-Glu-γ-D-Glu species, produced by a method in accordance with the first aspect of the invention or is prepared from said species.

In a further aspect, the invention provides a method for the preparation and purification of the trisodium salt of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid (ONX-0801) comprising the steps of:

(i) dissolution of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or a sub-stoichiometric sodium salt thereof, in an aqueous sodium base;

(ii) adjustment of the pH, if necessary;

(iii) column chromatography;

(iv) optionally, concentration of the product eluted from step (iii); and (v) lyophilization.

Preferably, the (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid used in step (i) is prepared by a method comprising the steps described for the first and/or second aspects of the invention.

In an additional aspect, the present invention provides compounds and intermediates, useful in the synthesis of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid and its trisodium salt, such as:

(R)-bis(trimethylsilyl) 2-((S)-5-(benzyloxy)-4-(benzyloxycarbonylamino)-5-oxopentanamido)pentanedioate;

(R)-2-((S)-5-(benzyloxy)-4-(benzyloxycarbonylamino)-5-oxopentanamido)pentanedioic acid;

(S)-1H-benzo[d][1,2,3]triazol-1-yl 4-((2-(hydroxymethyl)-4-oxo-4,6,7,8-tetrahydro-3H-cyclopenta[g]quinazolin-6-yl)(prop-2-ynyl)amino)benzoate;

(R)-bis(trimethylsilyl) 2-((S)-4-(4-(((S)-2-(hydroxymethyl)-4-oxo-4,6,7,8-tetrahydro-3H-cyclopenta[g]quinazolin-6-yl)(prop-2-ynyl)amino)benzamido)-5-oxo-5-(trimethylsilyloxy)pentanamido)pentanedioate;

(S)-1H-benzo[d][1,2,3]triazol-1-yl 4-((2-(trimethylsiloxymethyl)-4-oxo-4,6,7,8-tetrahydro-3H-cyclopenta[g]quinazolin-6-yl)(prop-2-ynyl)amino)benzoate;

(R)-bis(trimethylsilyl) 2-((S)-4-(4-(((S)-2-(trimethylsiloxymethyl)-4-oxo-4,6,7,8-tetrahydro-3H-cyclopenta[g]quinazolin-6-yl)(prop-2-ynyl)amino)benzamido)-5-oxo-5-(trimethylsilyloxy)pentanamido)pentanedioate.

Synthesis of L-Glu-γ-D-Glu

The present invention provides a method for the synthesis of a L-Glu-γ-D-Glu comprising the steps of:

a) activating the γ-carboxylic acid of an N-αO-diprotected L-Glu derivative;

b) silylating D-glutamic acid; and c) reacting the activated carboxylic acid derivative produced in step a) with the silylated product of step b) to give a fully protected L-Glu-γ-D-Glu species.

Step a)—Activation of a N-αO-Diprotected L-Glu Derivative

Step a) comprises activating the γ-carboxylic acid of an N-αO-diprotected L-Glu derivative.

In some embodiments, the N-αO-diprotected L-Glu derivative is a diprotected derivative of general formula:

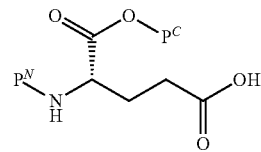

wherein $P^C$ is a carboxylic acid protecting group and $P^N$ is an amine protecting group.

Suitable carboxylic acid protecting groups are known in the art, for example those described in "Protective Groups in Organic Synthesis" 3rd Edn. TW. Greene and PGM Wuts Wiley New York, 1999. Pp 387-431, which is hereby incorporated by reference.

In some embodiments the α-carboxylic acid protecting group on the L-Glutamic acid derivative ($P^C$) is selected from: a benzyl or optionally substituted benzyl ester; an allyl ester; a t-butyl ester; or a 2-trimethylsilylethyl ester.

Suitable amine protecting groups are also known in the art, for example those described in "Protective Groups in Organic Synthesis" $3^{rd}$ Edn. T W. Greene and PGM Wuts Wiley New York, 1999. Pp 503-572, which is hereby incorporated by reference.

In some embodiments the amine protecting group on the L-Glutamic acid derivative ($P^N$) is selected from: a carbamate; a benzyl or optionally substituted benzyl carbamate, including but not limited to 4-methoxybenzyl carbamate; an allyl carbamate; a t-butyl carbamate; a 9-fluorenylmethyl carbamate; or a 2-trimethylsilylethyl carbamate.

In some preferred embodiments both the amine and the α-carboxylic acid of L-Glutamic acid are protected by groups ($P^N$, $P^C$), which can be removed in the same chemical step.

For example, use of an (optionally substituted) benzyl carbamate with the same or different optional substitution on a benzyl ester, allows both groups to be removed by hydrogenolysis. Use of an allyl carbamate with an allyl ester would allow both groups to be removed with catalytic palladium and a formate salt. Use of a t-butyl carbamate with a t-butyl ester would allow both groups to be removed under acidic conditions.

In preferred embodiments, the N-αO-diprotected L-Glu derivative is N-benzyloxycarbonyl-L-glutamic acid-α-benzyl ester or another suitable N-αO-diprotected L-Glu derivative.

In some embodiments, the N-αO-diprotected L-Glu derivative is N-benzyloxycarbonyl-L-glutamic acid-α-benzyl ester.

In some embodiments, activation comprises conversion of the γ-carboxylic acid of said N-αO-diprotected L-Glu derivative into an activated derivative.

In some embodiments, activation comprises conversion of the γ-carboxylic acid, N-benzyloxycarbonyl-L-glutamic acid-α-benzyl ester, into an activated derivative.

Various activated carboxylic acid derivatives and methods of making them are known in the art. Examples include acid chlorides, acid fluorides, acid anhydrides, both symmetric and asymmetric, O-acylureas, thioesters, activated esters such as p-nitrophenyl, and 1,O-oxybenzotriazole esters, activated amides such as N-acyl imidazoles, mixed anhydrides such as O-acylphosphonates and O-acylsulfonates and acyl azides. Many of these, and other activated carboxylic acids, as exemplified in "Peptide Synthesis; A Practical Handbook" M. Bodanszky Springer-Verlag 1993, are suitable for use in peptide synthesis reactions.

In some embodiments, the activated derivative is an anhydride.

In the anhydride is a mixed anhydride.

In some embodiments, activation comprises conversion of the N-αO-diprotected L-Glu derivative into an activated derivative, such as an anhydride. For example, an anhydride of formula:

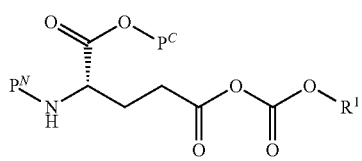

where $R^1$ is a $C_{1-4}$ alkyl group and $P^C$ and $P^N$ are as previously defined.

In some embodiments, activation comprises conversion of N-benzyloxycarbonyl-L-glutamic acid-α-benzyl ester into an activated derivative, for example an anhydride of formula:

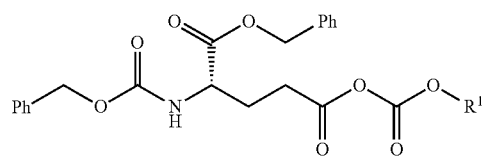

where $R^1$ is a $C_{1-4}$ alkyl group.

In some embodiments, $R^1$ is isobutyl.

In some embodiments, activation comprises treatment of the N-αO-diprotected L-Glu derivative, preferably N-benzyloxycarbonyl-L-glutamic acid-α-benzyl ester, with an alkyl chloroformate, for example $R^1OC(=O)Cl$.

In some embodiments, activation comprises treatment of the N-αO-diprotected L-Glu derivative, preferably N-benzyloxycarbonyl-L-glutamic acid-α-benzyl ester with an alkyl chloroformate and a tertiary amine base.

In some embodiments the chloroformate is isobutyl chloroformate.

In some embodiments, the tertiary amine base is N-methylmorpholine (NMM).

In some embodiments, activation comprises inverse addition of a solution of the N-αO-diprotected L-Glu derivative, preferably N-benzyloxycarbonyl-L-glutamic acid-α-benzyl ester, as a trialkylammonium salt, to a solution of the alkyl chloroformate at low temperature.

In some embodiments the N-αO-diprotected L-Glu derivative is added slowly to a low temperature solution of the alkyl chloroformate and tertiary amine base.

In some embodiments, the low temperature solution is at a temperature of about −10° C. to −50° C., preferably at a temperature of about −30° C.

In some embodiments the addition temperature is in the range −25 to −40° C.

In some embodiments, the ratio of the N-αO-diprotected L-Glu derivative (e.g. N-benzyloxycarbonyl-L-glutamic acid-α-benzyl ester) to the tertiary amine base to the chloroformate is around 1:1.2:1.1.

In some embodiments, the reaction is carried out in THF as solvent.

Step b)—Silylation of D-Glutamic Acid

Step b) comprises silylating D-glutamic acid.

in some embodiments, silylation comprises treatment of D-glutamic acid with a silylating agent.

In some embodiments, silylation comprises treatment of D-glutamic acid with a silylating agent to produce a silylated D-Glu species of formula:

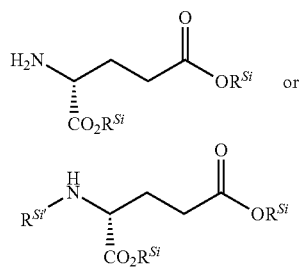

wherein each $R^{Si}$ and $R^{Si'}$ is independently a silyl protecting group, as defined below, and may be the same or different.

In some embodiments, all of the $R^{Si}$ and $R^{Si'}$ groups are the same silyl protecting group.

Various silyl protecting groups, and suitable silyating agents for their introduction, are known in the art (see, for example "Protective Groups in Organic Synthesis" $3^{rd}$ Edn. TW. Greene and PGM Wuts Wiley New York, 1999).

In some embodiments, $R^{Si}$ and $R^{Si'}$ are each independently selected from trimethylsilyl (—SiMe$_3$), triethylsilyl (—SiEt$_3$), t-butyldimethylsilyl (—Si$^t$BuMe$_2$), phenyldimethylsilyl (—SiPhMe$_2$), t-butyldiphenylsilyl (—Si$^t$BuPh$_2$) or triisopropylsilyl (—Si$^i$Pr$_3$).

In some embodiments, $R^{Si}$ is trimethylsilyl (—SiMe$_3$).

In some embodiments, $R^{Si'}$ is trimethylsilyl (—SiMe$_3$).

In some embodiments, $R^{Si}$ and $R^{Si'}$ are both trimethylsilyl (—SiMe$_3$).

In some embodiments, the silylating agent is O,N-bis-(trimethylsilyl)acetamide (BSA).

In some embodiments, the silylating agent is used in an amount of at least 3 molar equivalents relative to the D-glutamic acid.

In some embodiments the silyl group is chosen to form a silyl ester with a much higher degree of stability to hydrolytic and alcoholytic conditions than trimethylsilyl. For example, t-butyldimethylsilyl, phenyldimethylsilyl, t-butyldiphenylsilyl or triisopropylsilyl esters may be preferred, if it is intended to isolate the fully protected species and/or if it is desired to carry a silylated species through to any of the subsequent steps.

Step c)—Reaction of the Products of Steps a) and b)

Step c) comprises reacting the activated carboxylic acid derivative produced in step a) with the silylated product of step b) to give a protected L-Glu-γ-D-Glu species.

In some embodiments, the protected L-Glu-γ-D-Glu species is a fully protected L-Glu-γ-D-Glu species.

In some embodiments, the protected L-Glu-γ-D-Glu species is a compound of formula:

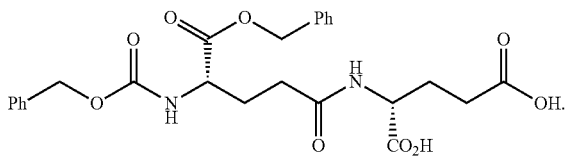

wherein $R^{Si}$ is a silyl protecting group.

In some embodiments, a solution of the silylated D-Glu species from step b) is added to a cold solution of the activated carboxylic acid derivative from step a).

In some embodiments, the solution of the silylated D-Glu species is added directly from the reaction mixture of step b).

In some embodiments, in step b), D-glutamic acid is solubilized with several equivalents of the silylating agent; then in step c), that solution is added to a cold solution of the carboxylic acid derivative from step a) to form a silyl esterified solution of 2R—(N—(S)-4-(benzyloxycarbonyl)-4-benzyloxycarbonylamino)-1-oxobutyl)amino)pentanedioic acid.

In some embodiments, the solvent is THF.

In some embodiments, in step b), D-glutamic acid is used in an amount of about 1.1 equivalents and in step c), the silylating agent is used in an amount of about 3.5 equivalents, relative to the amount of the N-αO-diprotected L-Glu derivative.

In some embodiments the method includes a work-up after the coupling step.

In some embodiments, the work-up does not cleave the silyl esters.

In some embodiments, the work-up comprises a de-silylating aqueous work-up.

In some embodiments, after reaction, the silyl esterified solution, comprising a 2R—(N—(S)-4-(benzyloxycarbonyl)-4-benzyloxycarbonylamino)-1-oxobutyl)amino)pentanedioic acid disilyl ester, preferably the O,O-bis(trimethylsilyl) ester, is subjected to a de-silylating aqueous work-up, to produce 2R—(N—(S)-4-(benzyloxycarbonyl)-4-benzyloxycarbonylamino)-1-oxobutyl)amino)pentanedioic acid in good yield and purity.

Hence, in some embodiments the protected L-Glu-γ-D-Glu species resulting from step (c) is a compound of formula:

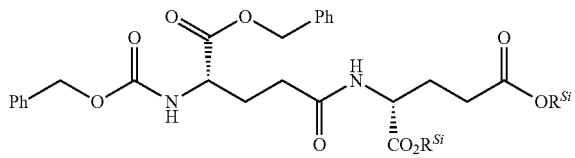

In some embodiments, the de-silylating work-up comprises aqueous organic partition, i.e. partition of the solution between water and an organic solvent.

In some embodiments, the organic solvent is ethyl acetate.

In some embodiments, the de-silylating work-up comprises addition of acid.

In some embodiments, acid is added to adjust the pH of the solution to about pH 2.

In some embodiments, after aqueous organic partition, acid is added to acidify the aqueous portion.

In some embodiments, the acid is hydrochloric acid.

In some embodiments, the work-up comprises solvent exchange.

In some embodiments, solvent exchange comprises solvent exchange to replace the initial solvent with a new solvent.

In some embodiments solvent exchange comprises removal of the first solvent e.g. by evaporation and/or azeotrope.

In some embodiments, the initial solvent is ethyl acetate.

In some embodiments, the new solvent is acetonitrile.

In some embodiments, the resultant protected L-Glu-γ-D-Glu species recrystallizes from the new solvent, to provide 2R—(N—(S)-4-(benzyloxycarbonyl)-4-benzyloxycarbonylamino)-1-oxobutyl)amino)pentanedioic acid in good yield and purity.

Step d)—Deprotection of the L-Glu-γ-D-Glu Species

In some embodiments, the method comprises a further step:
 d) deprotecting said protected L-Glu-γ-D-Glu species.

In some embodiments, deprotection comprises complete deprotection i.e. removal of all protecting groups from the protected L-Glu-γ-D-Glu species.

In some embodiments, deprotection comprises partial deprotection i.e. removal of only some of the protecting groups from the protected L-Glu-γ-D-Glu species.

For example, deprotection may comprise removal of the protecting groups on the L-Glu moiety, while leaving any silyl protecting groups on the D-Glu moiety, if present, intact.

In some embodiments, deprotection comprises removal of (optionally substituted) benzyl and/or benzyloxycarbonyl protecting groups, to produce L-Glutamyl-γ-D-Glutamic acid or a disilyl ester thereof.

In some embodiments, deprotection comprises removal of t-butyl and/or t-butyloxycarbonyl protecting groups to produce L-Glutamyl-γ-D-Glutamic acid.

In some embodiments, deprotection comprises removal of the benzyl and benzyloxycarbonyl protecting groups from 2R—(N—(S)-4-(benzyloxycarbonyl)-4-benzyloxycarbonylamino)-1-oxobutyl)amino)pentanedioic acid, to produce L-Glutamyl-γ-D-Glutamic acid.

In some embodiments, deprotection comprises removal of allyl and/or allyloxycarbonyl protecting groups to produce L-Glutamyl-γ-D-Glutamic acid or a disilyl ester thereof.

In some embodiments, deprotection comprises desilylation.

In some embodiments, deprotection comprises removal of 2-trimethylsilylethyl and/or 2-trimethylsilylethoxycarbonyl protecting groups, to produce L-Glutamyl-γ-D-Glutamic acid.

The conditions chosen for the deprotection step will depend on the protecting groups to be removed. Conditions for the removal of various amine and carboxylic acid protecting groups are known in the art (see "Protective Groups in Organic Synthesis" 3$^{rd}$ Edn. TW Greene and PGM Wuts Wiley New York, 1999, as above). If there is more than one type of protecting group to be removed, there may be more than one deprotection step.

In some embodiments deprotection comprises removal of protecting groups under acidic conditions, such as dissolution in TFA (trifluoroacetic acid).

In some embodiments deprotection comprises removal of protecting groups with fluoride ion, such as treatment with TBAF (tetrabutylammonium fluoride) or pyridine.HF complex.

In some embodiments, deprotection comprises hydrogenolysis.

In some embodiments deprotection comprises hydrogenolysis with a formate salt and an appropriate transition metal catalyst.

In some embodiments, deprotection comprises hydrogenolysis in aqueous ethanol, with an appropriate transition metal catalyst.

In some embodiments, the transition metal catalyst comprises a palladium on carbon catalyst.

In some embodiments, hydrogenolysis comprises use of hydrogen at 15-50 psi.

In some embodiments, hydrogenolysis is performed at room temperature.

In some embodiments, hydrogenolysis is performed at room temperature followed by warming to 60° C. In some embodiments, warming to 60° C. is followed by a hot filtration.

In some embodiments, deprotection comprises hydrogenolysis in aqueous ethanol, with an appropriate transition metal catalyst and the initial ratio of 2R—(N—(S)-4-(benzyloxycarbonyl)-4-benzyloxycarbonylamino)-1-oxobutyl) amino)pentanedioic acid to ethanol to water is about 1 gram:10 mL:2 mL.

In some embodiments, the initial ratio of 2R—(N—(S)-4-(benzyloxycarbonyl)-4-benzyloxycarbonylamino)-1-oxobutyl)amino)pentanedioic acid to ethanol to water is about 1 gram:7.9 gram: 7 grams.

In some embodiments, hydrogenolysis is followed by a work-up which allows the compound to be isolated in good yields as a crystalline solid.

In some embodiments, work-up comprises an initial filtration to remove Pd/C.

In some embodiments, after the initial filtration, the residue is rinsed with about 10 mL of ethanol and about 1 mL of water per gram of the starting material.

In some embodiments, work-up comprises heating.

In some embodiments, work-up comprises filtration.

In some embodiments, work-up comprises treatment with thiosilica, preferably at 60° C., followed by refiltration.

In some embodiments, work-up comprises allowing the material to crystallize out upon cooling.

In some embodiments, work-up comprises filtration and the initial filtration residue is rinsed with about 5-6 grams of ethanol per gram of the starting material.

In some embodiments work-up comprises filtration and the initial filtrate and rinsings are treated with thiosilica (preferably approximately 2 wt % based on starting material), preferably for 4 hours, preferably at 60° C. In some embodiments, the mixture is then refiltered hot. The filter residue is then preferably rinsed with further ethanol (e.g. about 2 grams/gram of starting material). The filtered solution is then preferably allowed to cool slowly to ambient temperature, and is then cooled to 5-10° C.

In some embodiments, the product is isolated as a crystalline solid containing about 5-15 wt % water.

In some embodiments, the product contains below about 10 ppm palladium.

Synthesis of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino) benzamido)-butanamido)pentanedioic acid The invention provides a method for the synthesis of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or a pharmaceutically acceptable salt or solvate thereof, comprising the step of coupling a protected L-Glu-γ-D-Glu species with (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid.

In some embodiments, coupling comprises activation of the carboxylic acid moiety of (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid, followed by treatment with a protected L-Glu-γ-D-Glu species.

In some embodiments, activation comprises conversion of (6S)-4,N-((2-(hydroxymethyl)-4-oxo-3,4,7,8-tetrahydro-3H-cyclopenta[g]quinazolin-6-yl)-N-(prop-2-ynyl)amino) benzoic acid into an activated carboxylic acid derivative, preferably an activated ester derivative.

Various activated carboxylic acid derivatives and methods of making them are known in the art, as previously discussed above.

In some embodiments, activation comprises conversion of (6S)-4,N-((2-(hydroxymethyl)-4-oxo-3,4,7,8-tetrahydro-3H-cyclopenta[g]quinazolin-6-yl)-N-(prop-2-ynyl)amino)

benzoic acid into an activated HOBT ester, for example by treatment with 1-hydroxybenzotriazole hydrate (HOBT) and a coupling reagent.

In some embodiments, the coupling agent is a diimide coupling agent.

In some embodiments, the coupling agent is EDCl (N-(3-(N,N-dimethylamino)propyl)-N'-ethylcarbodiimide hydrochloride)

In some embodiments conversion is carried out in THF.

In some embodiments conversion is carried out in acetonitrile (ACN).

In some embodiments conversion is carried out at a temperature of from about 0° C. to about 25° C.

In some embodiments, the activated carboxylic acid derivative is O-(1,N-benzotriazyl)(6S)-4,N-((2-(hydroxymethyl)-4-oxo-3,4,7,8-tetrahydro-3H-cyclopenta[g]quinazolin-6-yl)-N-(prop-2-ynyl)amino)benzoate.

In some embodiments, conversion comprises reaction of (6S)-4,N-((2-(hydroxymethyl)-4-oxo-3,4,7,8-tetrahydro-3H-cyclopenta[g]quinazolin-6-yl)-N-(prop-2-ynyl)amino) benzoic acid, hydroxybenzotriazole hydrate and N-(3-(N,N-dimethylamino)propyl)-N'-ethylcarbodiimide hydrochloride in molar ratios in the ranges of 1.0:1.1-1.3:1.1-1.5.

In some embodiments the loading of the cyclopenta[g] quinazolinyl acid is in the range of about 20 to about 40 grams/Liter.

In some embodiments an HPLC system is used to monitor in-process formation of the activated carboxylic acid derivative during the coupling reaction.

In some embodiments, the protected L-Glu-γ-D-Glu species is silyl protected L-Glutamyl-γ-D-Glutamic acid.

In some embodiments, the protected L-Glu-γ-D-Glu species is a compound of formula:

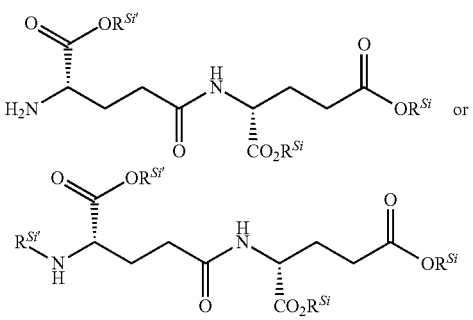

wherein each $R^{Si}$ and $R^{Si'}$ is a silyl protecting group, as previously defined, and may be the same or different.

In some embodiments, all of the $R^{Si}$ groups and $R^{Si'}$ groups are the same silyl protecting group.

In some embodiments, the silyl protecting group is trimethylsilyl (—SiMe$_3$).

In other embodiments, $R^{Si}$ and $R^{Si'}$ are different silyl protecting groups.

In some embodiments, each $R^{Si}$ is selected from t-butyldimethylsilyl, phenyldimethylsilyl, t-butyldiphenylsilyl or triisopropylsilyl and each $R^{Si'}$ is trimethylsilyl.

The silyl protected L-Glu-γ-D-Glu species is preferably produced by silylation of L-Glutamyl-γ-D-Glutamic acid.

In an alternative embodiment, the silyl protected L-Glu-γ-D-Glu species is produced by further silylation of a L-Glutamyl-γ-D-Glutamic acid disilyl ester.

In some embodiments, L-Glutamyl-γ-D-Glutamic acid, or a disilyl ester thereof, is prepared by a method of the invention as discussed above.

In some embodiments, silylation comprises treatment with a silylating agent.

In some embodiments, the silylating agent is O,N-bis (trimethylsilyl)acetamide.

In some embodiments, the silyl protected L-Glu-γ-D-Glu species is generated in situ by silylation and solubilization of L-Glutamyl-γ-D-Glutamic acid or the disilyl ester thereof, and the activated carboxylic acid derivative is added directly to the resulting solution.

In some embodiments, the silylating agent may be used to bring the unprotected dipeptide, L-Glutamyl-γ-D-Glutamic acid, into solution, thus allowing reaction to occur. It may also act as a general mild drying agent to suppress hydrolytic side reactions.

In some embodiments, the silylating agent present in the reaction mixture may additionally silylate the primary alcohol on the activated carboxylic acid derivative (i.e. the 2-hydroxymethyl group of the activated ester of (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid may become silylated, to produce a 2-silyloxymethyl group, preferably a 2-trimethylsilyloxy group), although this does not affect the subsequent coupling reaction.

The reaction mixture may therefore comprise a silylated activated ester such as, for example, (S)-1H-benzo[d][1,2,3]triazol-1-yl 4-((2-(trimethylsiloxymethyl)-4-oxo-4,6,7,8-tetrahydro-3H-cyclopenta[g]quinazolin-6-yl)-N-(prop-2-ynyl)amino)benzoate. The product of the coupling reaction may therefore comprise a fully silylated coupling product such as, for example, (R)-bis(O-trimethylsilyl) 2-((S)-4-(4-(((S)-2-(trimethylsiloxymethyl)-4-oxo-4,6,7,8-tetrahydro-3H-cyclopenta[g]quinazolin-6-yl)(prop-2-ynyl)amino)benzamido)-5-oxo-5 (trimethylsilyloxy)pentanamido) pentanedioate.

In some embodiments, solid L-Glutamyl-γ-D-Glutamic acid is added directly to a preformed solution of the activated carboxylic acid derivative, followed by the silylating agent.

In some embodiments, the reaction mixture, containing a slurry of L-Glutamyl-γ-D-Glutamic acid is cooled to about −5 to −10° C. prior to the addition of the silylating agent. Preferably, during the addition, and for some period of time after the addition, the temperature of the reaction mixture is not allowed to rise above 10° C.

In some embodiments, the silylating agent is added gradually. Preferably, any exotherm noted upon addition is carefully controlled.

In some embodiments, the silylating agent is used in an amount of about 7-10 molar equivalents.

In some embodiments, the solvent for this process is acetonitrile.

In some embodiments, solid L-Glutamyl-γ-D-Glutamic acid is added directly to a pre-formed solution of the activated carboxylic acid derivative, after addition of the silylating agent.

In some embodiments, the silylating agent and L-Glutamyl-γ-D-Glutamic acid are reacted together in a separate reactor, prior to addition to a pre-formed solution of the activated carboxylic acid derivative.

In some embodiments, reaction of the silylating agent and L-Glutamyl-γ-D-Glutamic acid is performed in THF for a period of 2-24 hours at 20-25° C., In some embodiments, the coupling reaction is monitored by in-process HPLC.

Preferably, work-up is initiated once the intermediate O-benzotriazol-1-yl (6S)-4,N-((2-(hydroxymethyl)-4-oxo- 3,4,7,8-tetrahydro-3H-cyclopenta[g]quinazolin-6-yl)-N-(prop-2-ynyl)amino)benzoate is ≥99% consumed.

In some embodiments, the molar ratio of (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid to L-Glutamyl-γ-D-Glutamic acid is in the range 1:1.2-1.5.

In some embodiments the water content of (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid is in the range 0-4% by weight.

In some embodiments, the water content of L-Glutamyl-γ-D-Glutamic acid is in the range of 5-15% by weight.

In some embodiments, the water content of L-Glutamyl-γ-D-Glutamic acid is in the range of 9-12% by weight.

In some embodiments, a pre-formed solution of the activated carboxylic acid derivative is added to an in situ generated L-Glutamyl-γ-D-Glutamic acid polysilylated ester.

Coupling of the activated carboxylic acid derivative to a silyl protected L-Glu-γ-D-Glu species produces silylated (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid.

In some embodiments, the crude solution of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid is initially purified using physical, phase based methods, such as precipitation or liquid-liquid extraction techniques In some embodiments, initial purification of (2,R)-((4,S)-carboxy-4-(4,N-(465)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid comprises exchanging the reaction solvent, preferably by stripping the reaction mixture under reduced pressure, and reconstituting with an alternative solvent.

In some embodiments, the reaction solvent is THF.

In some embodiments, the alternative solvent is an aqueous sodium base such as sodium bicarbonate, sodium carbonate or sodium hydroxide.

In some embodiments, an aqueous weakly alkaline (pH 7-10) solution thus produced is washed multiple times with a solvent of low water miscibility to remove many of the organic impurities. In some embodiments the washing solvent is ethyl acetate.

In some embodiments an aqueous, weakly alkaline, (pH 7-10) solution thus produced is first rinsed with a low aqueous miscible organic solvent such as ethyl acetate, and is then further purified by ultrafiltration.

In some embodiments, said rinsing and/or ultrafiltration is followed by sparging e.g. with nitrogen or other inert gas, or by limited evaporation under reduced pressure, to reduce the amounts of organic solvents present.

In some embodiments, a purified aqueous solution obtained from the above process may be used to load the product onto a chromatography column, for example as described below for the third aspect.

In some embodiments, an aqueous solution produced from the above process is acidified to precipitate (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, which is collected and dried. Aqueous formic acid may be a preferred acid for this precipitation, as it has very low propensity to be entrained in the precipitate. This product may then be redissolved in a dilute aqueous sodium base and chromatographed, for example as described below for the third aspect.

In some embodiments, the alternative solvent is acetonitrile.

In some embodiments, the reaction solvent is acetonitrile, in which case no solvent exchange may be required.

In some embodiments, initial purification of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid involves filtering the reaction mixture in acetonitrile.

In some embodiments, purification then involves further cooling the filtrate to 0 to 5° C., preferably whilst diluting it further with acetonitrile In some embodiments, the final ratio of acetonitrile to (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid, is 80-120 L/kg, In some embodiments, purification of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid further comprises precipitation.

In some embodiments, precipitation comprises addition of measured small quantities of an aqueous phase. This aqueous phase may be simply water, or it may be of higher pH, for example an aqueous sodium base such as saturated sodium bicarbonate solution, or it may be of lower pH, for example 2M formic acid solution. Preferably these are added slowly to the cold stirring reaction mixture. Preferably addition is followed by stirring for several hours at that temperature. In some embodiments, this is followed by vacuum filtration, preferably performed whilst still cold, under nitrogen.

In some embodiments, crude (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or a substoichiometric sodium salt thereof, is isolated as a free-flowing solid. In some embodiments, the amount of water, aqueous formic acid solution or aqueous sodium base solution used is in the range of about 0.8-1.0 grams/gram of (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid used in the coupling reaction.

For example, a method to desilylate and isolate (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid in greatly purified form may involve: filtration of the reaction mixture, dilution with further acetonitrile to produce a solution whereby there is approximately one liter of acetonitrile for every 10 grams of starting acid, (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid, followed by the slow addition of limited amounts of water, aqueous formic acid solution, preferably 2 M, or aqueous sodium bicarbonate solution, preferably saturated, around 10 mL/liter of acetonitrile, to the chilled, stirred reaction solution, followed by collection of the resultant precipitate, under a nitrogen atmosphere, and then drying in a vacuum oven at room temperature.

In some embodiments, the reaction mixture throughout the process, from BSA addition until collection of the solid precipitate, or aqueous quenching of the reaction mixture, is kept below 10° C.

Preparation of the trisodium salt of ONX-0801

The invention further provides a method for the preparation and purification of the trisodium salt of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid (ONX-0801) comprising the steps of:
  (i) providing a solution of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or a substoichiometric sodium salt thereof, in an aqueous sodium base;
  (ii) adjustment of the pH, if necessary;
  (iii) column chromatography;
  (iv) optionally, concentration of the product eluted in step (iii); and
  (v) lyophilization.

Step (i)—Formation of the Trisodium Salt

The trisodium salt is formed by treatment of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid with an appropriate sodium base. In some embodiments the sodium base is an aqueous sodium base.

Step (i) therefore comprises provision of a solution of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid in an aqueous sodium base.

In some embodiments, the trisodium salt is formed by dissolution of the acid, or a substoichiometric sodium salt thereof, in an aqueous sodium base, for example aqueous sodium carbonate or sodium bicarbonate solution.

In some embodiments, the trisodium salt is formed by dissolution of solid (2,R)-((4S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or a substoichiometric sodium salt thereof, preferably crude solid (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid or a substoichiometric sodium salt thereof.

In some embodiments, (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid may have been prepared as a solution in an aqueous sodium base and can therefore be used directly in steps (i) to (v).

Preferably, the (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or solution thereof, used in step (i) is prepared by a method comprising the steps described for the first and/or second aspects of the invention.

For example, solid (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or a substoichiometric sodium salt thereof, may be precipitated from the coupling reaction of the second aspect, as described above. Alternatively, an aqueous solution of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid may be obtained from the coupling reaction of the second aspect, after solvent exchange with an aqueous sodium base solution, as described above.

In some embodiments, in step (i), an aqueous sodium base solution is added directly to the reaction mixture after production of (2,R)-((4,S)-carboxy-4-(4,N-(((6S)-2-(hydroxymethyl)-4-oxo-3,4,7,8-tetrahydro-3H-cyclopenta[g]quinazolin-6-A-N-(prop-2-ynyl)amino)benzamido)butanamido)pentanedioic acid, e.g. to quench the reaction. This solution may be washed in various ways as described above.

In some embodiments, in step (i), crude precipitated (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or a substoichiometric sodium salt thereof, is added to a stirred cold aqueous solution of dilute sodium bicarbonate or sodium carbonate, and preferably stirred until all of the solid dissolves.

Step (ii)—Adjustment of the pH

In some embodiments, the pH of the solution produced in step (1) is adjusted to be in the pH 7.5-9.0 range.

In some embodiments the pH is adjusted to pH 8-9.

In some embodiments, the pH is adjusted by addition of sodium hydroxide.

Step (iii)—Column Chromatography

An aqueous solution of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid trisodium salt is purified by column chromatography on a suitable resin chromatography system.

In some embodiments, the chromatography system comprises a resin column.

In some embodiments, the resin is a modified polystyrene resin.

In some embodiments, the resin is selected from e.g. SP207SS and HP20SS.

In some embodiments, chromatography comprises eluting with water, or water containing 1-10% of a water-miscible solvent.

In some embodiments, the water-miscible solvent is THF or acetonitrile.

In some embodiments, chromatography comprises initially eluting with water, followed if required by a stepwise gradient of from 2% to no more than 10% acetonitrile in water.

In some embodiments, an aqueous solution containing the trisodium salt at a nominal concentration of about 40-50 mg/mL is loaded onto the column.

In some embodiments, the aqueous solution containing the trisodium salt, produced in step (i) or (ii) is loaded directly onto the column.

In some embodiments, the nominal loading of the trisodium salt on the resin is between 1:40 and 1:100 wt:wt.

In some embodiments, the nominal loading of the trisodium salt on the resin is between about 1:50 and about 1:60 wt:wt In some embodiments, the column after loading is eluted with water.

In some embodiments, the column after loading is eluted with at least 10 column volumes of water before elution with 2% acetonitrile in water.

In some embodiments, the column after loading is eluted only with water.

In some embodiments, all fractions with sufficient purity are combined to produce a final product of between 99.0 and 99.7% purity.

In some embodiments, the pH of the solution is adjusted upwards at this stage, for example if it is found to be below pH 7.

In some embodiments pH adjustment is performed by addition of aqueous sodium carbonate or sodium hydroxide solution.

In some embodiments, column fractions and/or pooled column fractions are stored between 0 and 10° C.

Step (iv)—Concentration of the Chromatography Product

In some embodiments, step (iv) comprises concentration of the product eluted from the chromatography in step (iii).

After chromatography, the collected fractions comprise a dilute aqueous solution of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid trisodium salt In some embodiments, after chromatography, the collected fractions are concentrated, using a technique which concentrates the solution whilst ensuring minimal loss of material and minimal degradation.

In some embodiments, after chromatography, the collected fractions are concentrated, for example using a continuous evaporation technique such as a wiped film evaporator; or using membrane based concentration processes such as ultrafiltration, diafiltration, nanofiltration, or reverse osmosis; or catch-and-release type affinity columns; or column loading and stripping.

In some embodiments, this concentration is carried out in an ultrafiltration apparatus, preferably using a membrane such as a 5 Pall Centrasette 0.65 Kd cut-off filter membrane.

In some embodiments, the temperature of the ultrafiltration apparatus is kept below 10° C.

In some embodiments, the pooled column fractions are concentrated between threefold and fifteenfold before the lyophilization step.

In some embodiments, the pooled column fractions are concentrated between eightfold and twelvefold before the lyophilization step.

In some embodiments the concentrated solution after ultrafiltration is diafiltered in the ultrafiltration apparatus with variable volumes of water. That is, the solution is rediluted with water by a factor of e.g. twofold to threefold, and then reconcentrated back to the initial volume, in order to reduce the amount of solvent or other water-soluble low molecular weight impurities in the aqueous solution. This treatment may be repeated more than once. This treatment may be performed at a temperature of from 0 to 10° C.

In some embodiments, before lyophilization, the concentrated solution is filtered for endotoxin removal. In some embodiments, this filtration is carried out through a 5000 MW cut-off filter, such as a Pellicon 2 maxi cassette 5000 MW cut-off filter.

Step (v)—Lyophilization

In a final step, lyophilization of the (optionally concentrated) solution gives (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid trisodium salt as a robust, but deliquescent lyophilization cake.

In some embodiments lyophilization is carried out using a shelf lyophilizer.

In some embodiments solutions containing about 3-50 mg/mL of (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid trisodium salt are used for the lyophilization step.

In some embodiments, the solution(s) are frozen to the range of −30 to −65° C., and exposed to a vacuum of 20-200 mtorr for 10-30 hours, with a shelf temperature of −15 to −25° C.

In some embodiments, the shelf temperature is then allowed to rise to about −15° C., and the vacuum is adjusted to about 20-80 mtorr for 1-10 days depending on the scale.

In some embodiments, the shelf temperature is then raised to −5° C. for at least a day.

In some embodiments, intermediate drying is carried out with a shelf temperature of 0° C., In some embodiments, final drying is carried out with a shelf temperature of +20° C., and the vacuum is adjusted to 10-25 mtorr.

In some embodiments, drying is continued until Karl Fischer water determination shows that the process is completed.

In some embodiments, the final lyophilization step produces a stable lyophilization cake, containing 1-5 wt % water.

In some embodiments, the lyophilization cake contains not more than 10% water by weight.

Compounds

The following compounds and intermediates, useful in the synthesis of (2,R)-((4,S)-carboxy-4-(4,N-(((6S)-2-(hydroxymethyl)-4-oxo-3,4,7,8-tetrahydro-3H-cyclopenta[g]quinazolin-6-A-N-(prop-2-ynyl)amino)benzamido)butanamido)pentanedioic acid and its trisodium salt, are provided:

i)

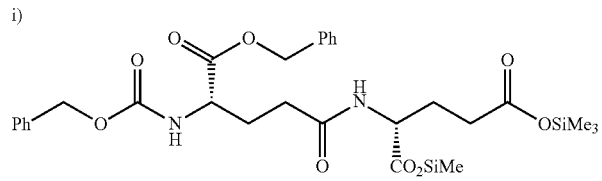

ii) (R)-bis(trimethylsilyl) 2-((S)-5-(benzyloxy)-4-(benzyloxycarbonylamino)-5-oxopentanamido)pentanedioate;

iii)

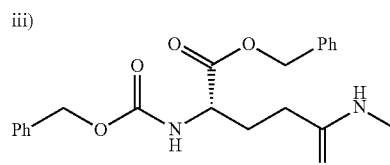

iv) (R)-2-((S)-5-(benzyloxy)-4-(benzyloxycarbonylamino)-5-oxopentanamido)pentanedioic acid;

v)

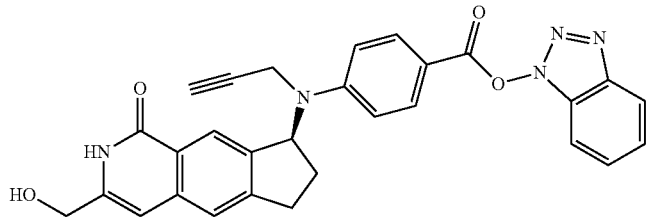

vi) (S)-1H-benzo[d][1,2,3]triazol-1-yl 4,N-((2-(hydroxymethyl)-4-oxo-4,6,7,8-tetrahydro-3H-cyclopenta[g]quinazolin-6-yl)-N-(prop-2-ynyl)amino)benzoate;

vii)

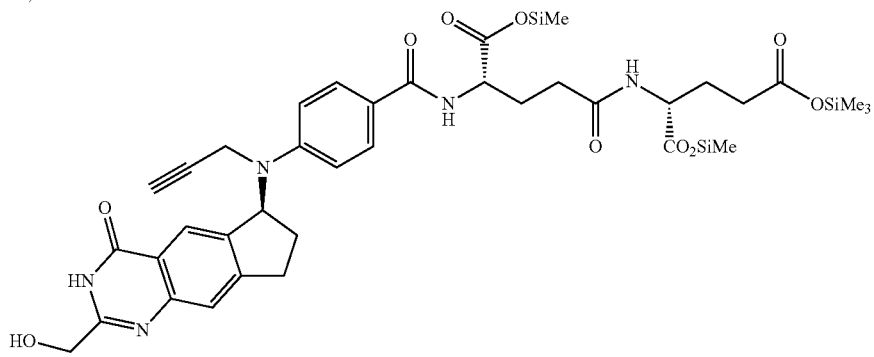

viii) (R)-bis(trimethylsilyl) 2-((S)-4-(4-(((S)-2-(hydroxymethyl)-4-oxo-4,6,7,8-tetrahydro-3H-cyclopenta[g]quinazolin-6-yl)-N-(prop-2-ynyl)amino)benzamido)-5-oxo-5-(trimethylsilyloxy)pentanamido)pentanedioate;

24 ix)

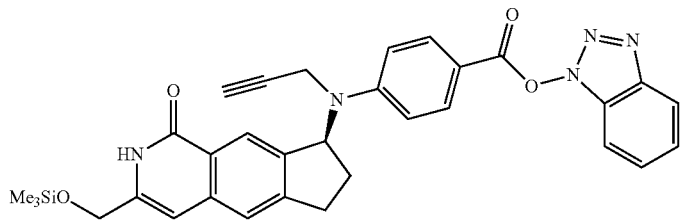

x) (S)-1H-Benzo[d][1,2,3]triazol-1-yl-4((2-(trimethylsiloxymethyl)-4-oxo-4,6,7,8-tetrahydro-3H-cyclopenta[g]quinazolin-6-yl)-N-(prop-2-ynyl)amino)benzoate 24;

25 xi)

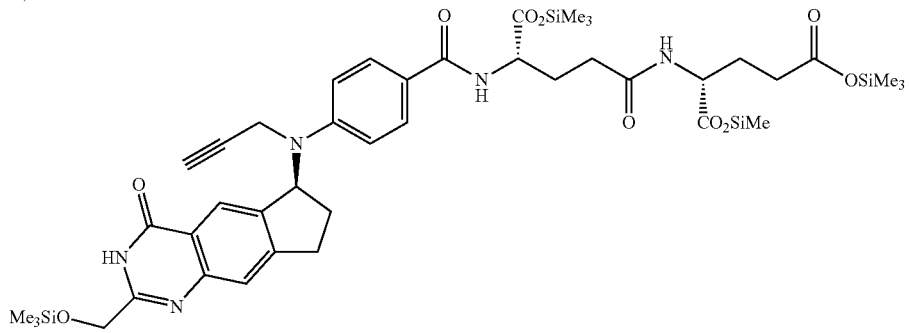

xii) (R)-Bis(trimethylsilyl) 2-((S)-4-(4-(((S)-2-(trimethylsiloxymethyl)-4-oxo-4,6,7,8-tetrahydro-3H-cyclopenta[g]quinazolin-6-yl)-N-(prop-2-ynyl)amino)benzamido)-5-oxo-5-(trimethylsilyloxy)pentanamido)pentanedioate. 25

DISCUSSION AND EXAMPLES

The present inventors have provided cost-effective and efficient synthetic methodologies for the preparation, isolation, and purification of 2 from (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid 7(S) and the simple dipeptide L-Glu-γ-D-Glu 15, produced in two steps from D-Glu 12 and a relatively inexpensive protected L-Glu derivative, such as Cbz-L-glutamic acid-α-benzyl ester 16.

For example, the chemistry described in Scheme 4, below, represents a preferred embodiment of the invention, and provides an efficient and scalable method of making L-Glutamyl-γ-D-Glutamic acid 15, which greatly reduces the cost of the peptide moiety of compounds 1 and 2. It then converts dipeptide 15 and (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid 7S into (2,R)-((4,S)-carboxy-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid trisodium salt 12 in a form suitable for formulation as a parenteral medication.

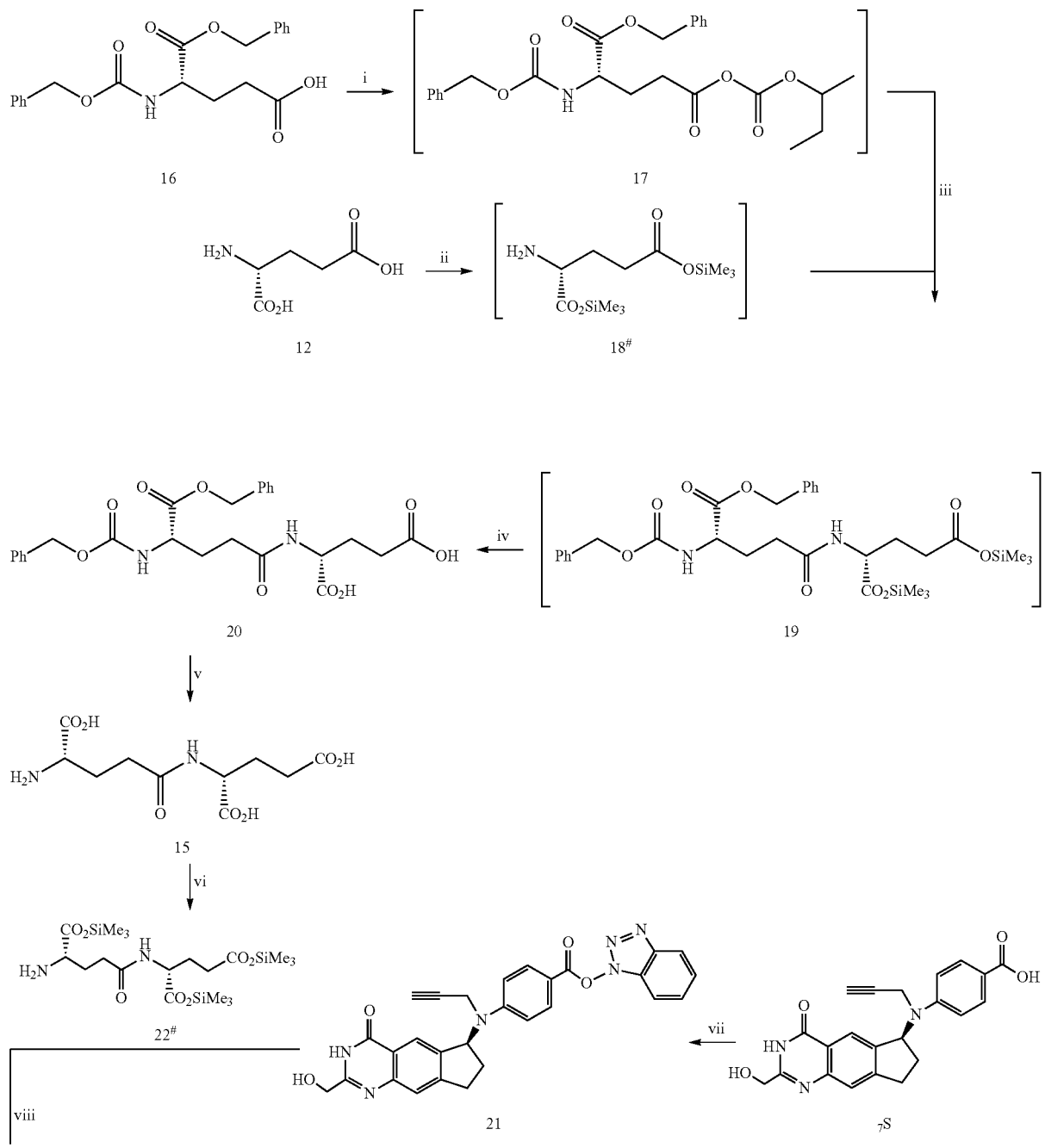

Scheme 4. Process of the invention for an efficient synthesis of Compound 2

-continued

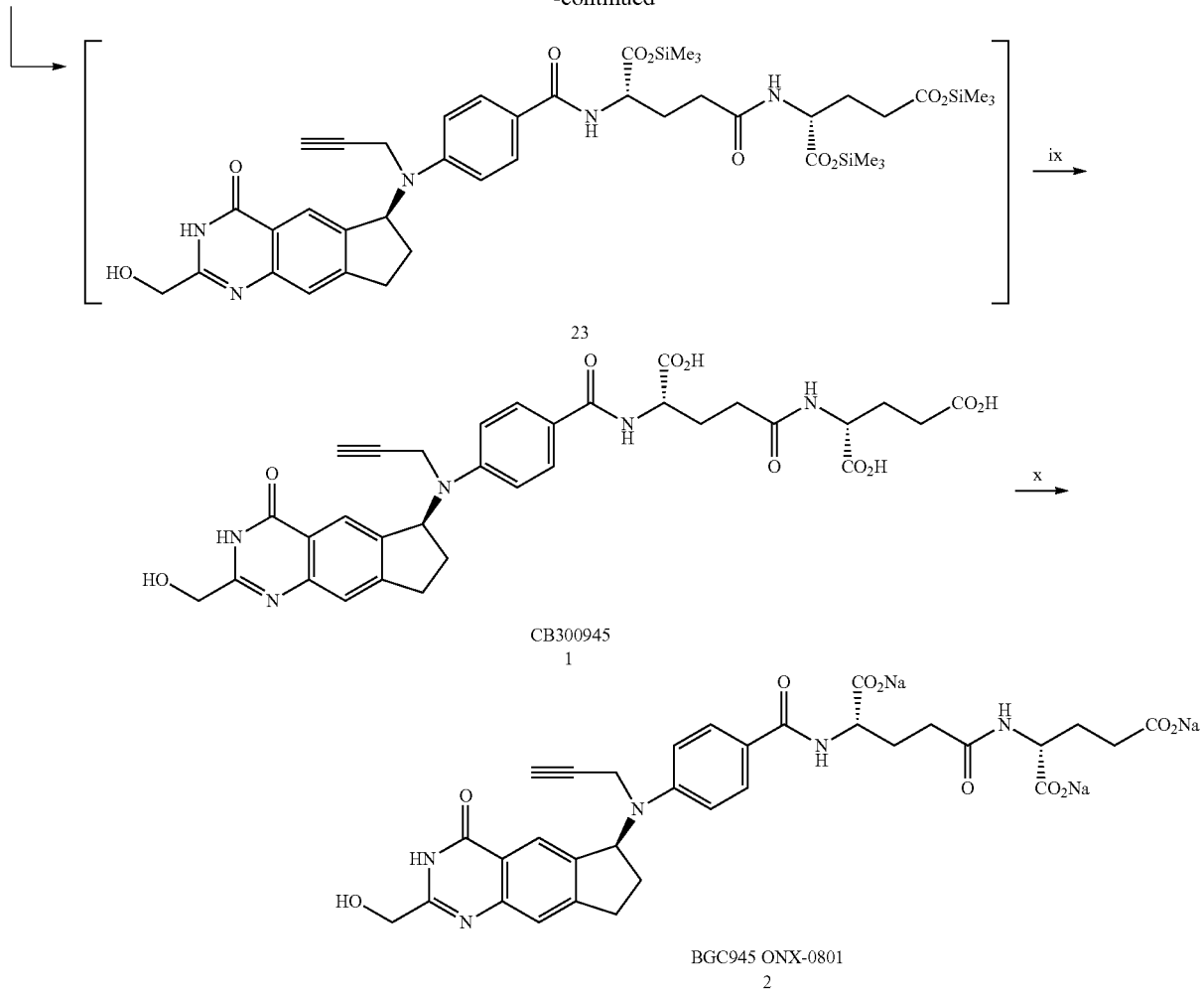

(i) NMM IBCF THF -30° C. (ii) BSA THF (iii) Add 18 to 17 -30 to 20° C. (iv) EtOAc water pH2 reX ACN (v) H2 Pd/C EtOH/H2O (vi)/(viii) Add 15 then BSA to preformed 21 (vii) EDC1 HOBT ACN (ix) H2O NaHCO3 (x) NaHCO3 water HP20SS resin # This intermediate may also be N-trimethylsilylated The chemistry described for this latter coupling and isolation is straightforward to carry out when optimized, circumvents a step which would be very difficult or impossible to run on a multi-kilo scale, and leads to a significant (>2-fold) increase in yield over previous preparations of 2, as well as removing a chromatography and the need to carry out one extra isolation and reaction. It may also make the whole sequence more readily monitored and controllable than previous processes, as well as greatly reducing the overall cost of these steps.

The process consists of two peptide couplings, both facilitated by the use of O,N-bis-(trimethylsilyl)acetamide, (BSA), or other appropriate silylating agents, in situ deprotections of silyl esters during isolation and purification, a hydrogenolytic debenzylation, and a single chromatography, for example on a modified polystyrene resin, followed by a lyophilization to give compound 2 as a storage-stable lyophilization cake, suitable for direct use in various drug product formulations.

The γ-carboxylic acid of N-benzyloxycarbonyl-L-glutamic acid-α-benzyl ester 16 is activated e.g. by conversion into a mixed anhydride such as 17, preferably using isobutyl chloroformate. In a separate vessel D-glutamic acid 12 is converted into a silyl ester, for example its bis-trimethylsilyl ester 18 (and possibly also N-trimethylsilylated) by extended treatment with BSA, or other appropriate silylating agent. The two solutions are mixed, and when the reaction is complete, the intermediate fully protected dipeptide 19 is subjected to a desilylating aqueous work-up, to give the desired di-protected L-Glu-γ-D-Glu derivative 20, which is isolated directly from the reaction mixture and recrystallized to high purity, and can be conveniently stored.

Compound 20 can be conveniently deprotected to the parent dipeptide L-Glutamyl-γ-D-Glutamic acid 15, by catalytic hydrogenation, and compound 15 can also be stored if desired. To complete the sequence N-cyclopentaquinazolin-6-yl aminobenzoic acid 7S is activated on the carboxylic acid, preferably by conversion to its 1-oxybenzotriazole ester 21, and this is then reacted with 22, the tris-trimethylsilyl ester of 15, which may have been made in another vessel and not isolated, or which may be generated in situ.

When the reaction is completed, no attempt need be made to isolate the (presumably) tris-silylated intermediate 23, but it can be worked up in a manner where either free acid 1, a substoichiometric sodium salt thereof, or trisodium salt 2 is directly isolated from the work-up. The final purification of the compound is carried out on trisodium salt 2 in an aqueous medium, and the purified salt 2 is isolated by Scheme 4a.

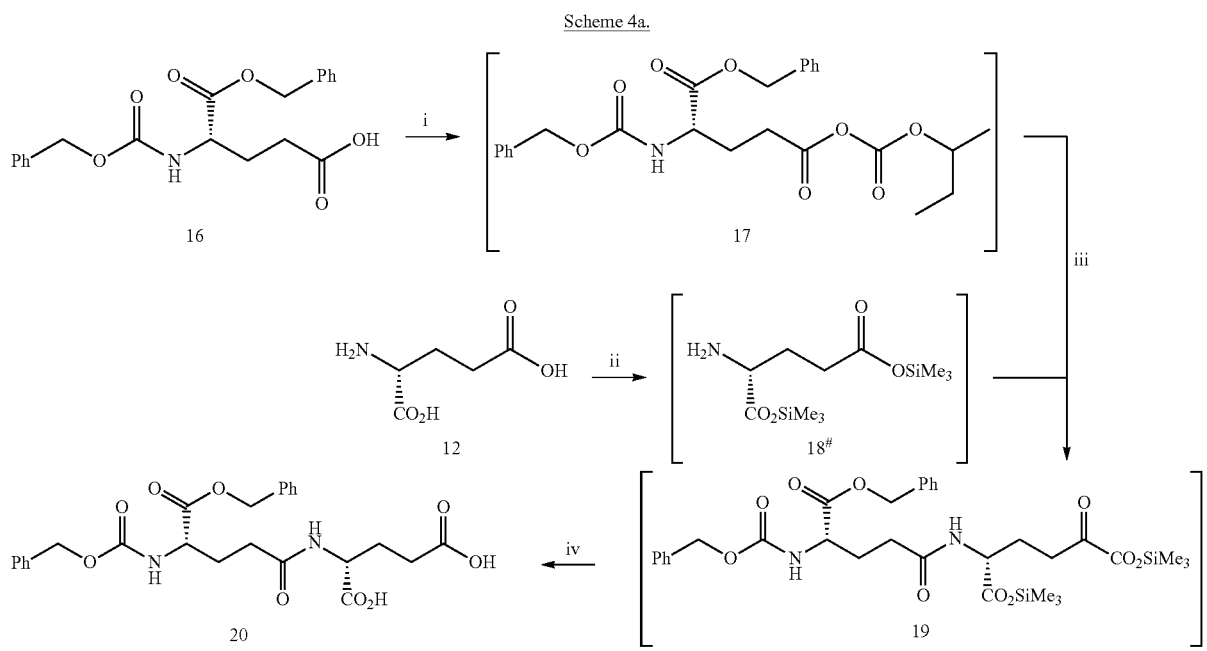

(i) NMM IBCF THF -30° C. (ii) BAS THF 20° C. (iii) Add 18 to 17 -30 TO 20° C. (iv) EtOAc water pH2 reX ACN # This intermediate may also be N-trimethylsilylated A non-limiting example of a preferred embodiment of the method of the invention is discussed in more detail below.

A suspension of D-glutamic acid in dry THF may be stirred under nitrogen at room temperature, and 3.5 equivalents of a silylating agent such as BSA added dropwise over 5-15 minutes. The solid dissolves gradually, forming the bis-trimethylsilyl ester 18, and possibly also silylating the amine nitrogen. The stirring is continued for 24-28 hours at room temperature. In a second vessel, 0.9 of an equivalent (based upon D-Glu) of N-benzyloxycarbonyl-L-glutamate-α-benzyl ester is stirred under nitrogen at room temperature until all of the solid has dissolved up, whereupon the solution is cooled to around −25° C. and about 1.2 equivalents of a tertiary amine base such as N-methylmorpholine is added, to form a salt.

This cold salt solution may then be inversely added slowly to a −30° C. solution of a coupling agent, preferably isobutyl chloroformate, also in THF, stirred under nitrogen. The inverse addition may decrease the amount of N-benzyloxycarbonyl-L-glutamoyl-α-benzyl ester anhydride formed in this reaction. Without wishing to be bound by theory reaction of acid 16 with isobutyl chloroformate might produce larger amounts of the symmetric anhydride, which may increase as the reaction scale increases. Although this symmetric anhydride forms the desired compound in the next step, the molecule of 16 released when the symmetric anhydride acylates D-Glu would end up as unreacted starting material, reducing the yield of the overall reaction, and so conditions (e.g. inverse addition) are preferably chosen to reduce this.

Once acid 16 has been completely converted to the mixed anhydride 17, the bis-silyl ester of D-Glu 18 is added to the reaction mixture slowly enough, to avoid any appreciable rise in temperature. After some additional time at low temperature, the reaction mixture is allowed to warm up slowly to room temperature, and is then stirred at that temperature for several hours to allow the reaction to go to completion.

The solution of the disilyl ester dipeptide 19 is then partitioned between water and ethyl acetate, and the aqueous phase is acidified, for example to about pH 2. This completely decomposes any silyl esters present, and ensures that the 20 produced is in the free acid form, which will be soluble in the organic phase, whilst any remaining D-Glu is partitioned into the aqueous phase. The phases are separated, and the organic phase may be rinsed a couple of times. The organic phase should contain mainly desired product 20 and a minor amount of unreacted starting N-Cbz-L-Glu O-benzyl ester 16. Most of the solvent can then be removed, and the remainder may be azeotroped out with acetonitrile. The resultant slurry may then be recrystallised from acetonitrile, in which the less polar starting ester 16 has moderate solubility. The recrystallised diprotected diglutamate 20 can be obtained in this single sequence in 80-85% yield, and 99% purity, making for a very efficient one step glutamoylation of 16 using the least expensive available source of D-glutamic acid, i.e. the acid itself.

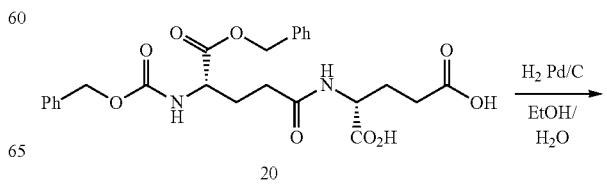

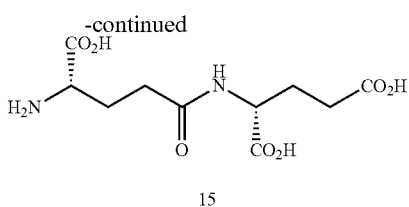

15

The double hydrogenolysis of N-benzyloxycarbonyl O-benzyl ester 20 to give unprotected L-glutamoyl-γ-D-glutamic acid 16 is straightforward, and a highly precedented chemical reaction. However, there is a great difference in physical properties between the starting material and the product, where the loss of the two lipophilic benzyl groups from water-insoluble 20 leads to a highly polar and acidic dipeptide 16, which is very water soluble but does not have good solubility in most organic solvents.

As the hydrogenolysis uses a heterogeneous catalyst, it is preferred that the substrate has reasonable solubility in the reaction medium, for the reaction to occur. The product preferably does not precipitate on the catalyst, as that may stop the reaction. Furthermore, the most practical way to separate the catalyst from the product is filtration so, preferably, all of the product 16 is in solution. High purity should be ensured, because this compound is very close to the final API. Use of aqueous ethanol is preferred as it suppresses unwanted esterification and allows for complete dissolution of the product on moderate heating, which allows for the catalyst to be removed by filtration. Preferred ratios of water to ethanol for the hydrogenation do not dissolve up all of the starting material, but allow for sufficient starting material to be in solution for the hydrogenation to proceed at a reasonable rate. They also allow for sufficient solubility of the product in the reaction mixture, such that it does not precipitate on the catalyst, which would inactivate the catalyst and stop the reaction. Furthermore, the aqueous ethanol mixture chosen suppresses the unwanted formation of ethyl ester side products.

It was also found that after filtration, addition of further ethanol to the mixture and heating to reform a solution allowed for a crystallization to occur, which directly recovers dipeptide 16 in very good purity and yield.

Furthermore, treating the warm, precrystallization, solution with 2% thiosilica gel, to scavenge remaining palladium prior to the polishing filtration, produces dipeptide 16 with acceptably low palladium levels (<5 ppm).

After the precipitation, dipeptide 16 contains a considerable amount of water, which could be deleterious in the next reaction (see below). However, attempting to lower the water content below about 8%, even using relatively mild drying conditions (45° C., vacuum oven with nitrogen bleed) may lead to the formation of dehydration products, as measured by mass spectrometry, where M-18+ ions appear. If present, these products may couple in the next reaction, and unique M-18+ ions then show up in the final coupling product, and may be difficult to separate from the desired product. Therefore, drying is preferably carried out with care, avoiding elevated temperatures, and it has been found that a water content of 9-14 wt % of water allows for optimal use in the next step, without generating detectable amounts of these dehydration products.

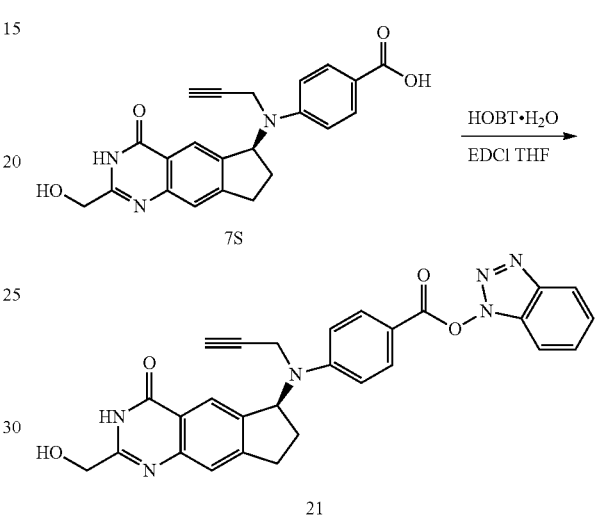

In the first part of the last step of this reaction sequence, a coupling agent such as EDCl (1.1-1.25 molar equivalents) is added to a solution of 6(S)-4,N-((2-(hydroxymethyl)-4-oxo-3,4,7,8-tetrahydro-3H-cyclopenta[g]quinazolin-6-yl)-N-(prop-2-ynyl)amino)benzoic acid 7S (preferably containing 0.5-5% by weight water) in a solvent such as THF or acetonitrile, containing a slurry of 1-hydroxybenzotriazole hydrate (HOBT.H$_2$O) (1.25-1.5 molar equivalents) stirred in a reactor at 20-25° C.

Over a period of 12-18 hours HPLC analysis demonstrates that complete conversion of acid 7S to HOBT ester 21 has occurred. Surprisingly, this reaction does not require any exogenous base to be added, and removal of the customary tertiary amine, or other weak base from this process has been shown to considerably increase the purity of the final product.

Scheme 4b. # This intermediate may also be trimethylsilylated

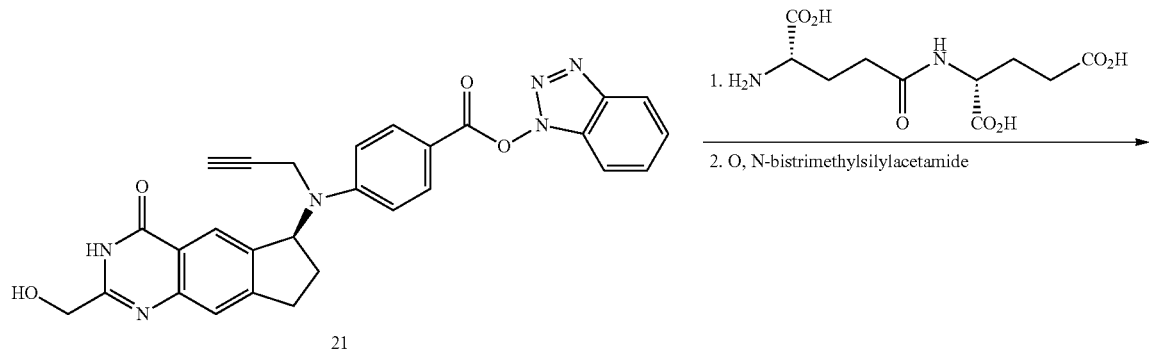

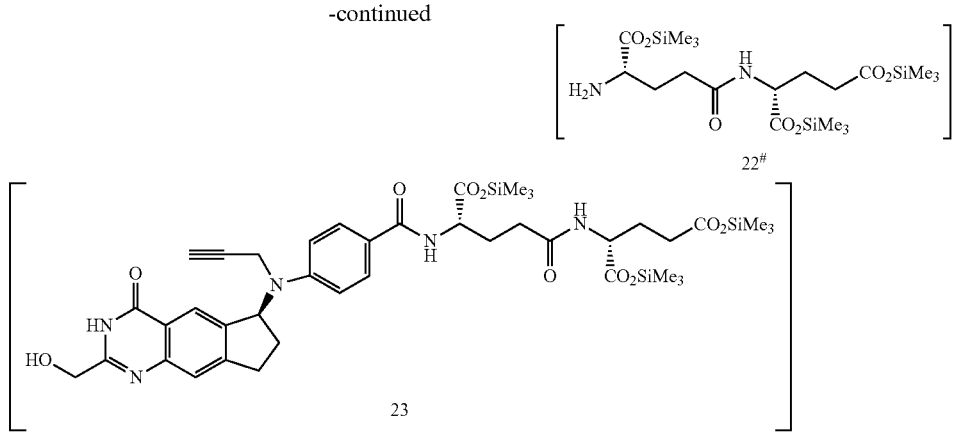

In the second step of this final reaction sequence, as soon as the in-process HPLC has shown >99% conversion of acid 7S to HOBT ester 21, solid L-Glu-γ-D-Glu 16 (1.5-2.0 molar equivalents) may be added directly in one portion to the thick slurried reaction mixture. The dipeptide is completely insoluble in acetonitrile, and forms a thick white slurry and HPLC analysis shows that no reaction occurs. This slurry is then cooled to −5 to −10° C., and O,N-bis-trimethylsilylacetamide (BSA)(8-10 molar equivalents) is run in over a period of 10-30 minutes (perhaps longer, depending on scale), at a rate which ensures that the reaction temperature does not exceed 10° C. A moderate exotherm is noted, and most of the solid gradually dissolves up. HPLC analysis shows disappearance of the HOBT ester 21, and a single major new peak appears.

Without wishing to be bound by theory, it is assumed that the BSA solubilizes dipeptide 16 as its tris-trimethylsilyl ester 22, although the reaction species may be wholly or in part a soluble lower silyl ester of 16, or possibly even the N-silyl derivative of tris-ester 22. Alternatively, tris-silyl ester 22 may be preformed in another reactor, by reaction of dipeptide 16 with BSA (8-10 molar equivalents) in acetonitrile. Once all of the solid has gone into solution, the solution of 22 is pumped into the solution of 21. This process uses more solvent and equipment than the first described process.

Immediately upon completion of the addition of BSA, the reaction mixture is held at 10° C. or slightly less until in process HPLC shows that the reaction is ≥99% complete by disappearance of ester 21, and at that time, probably 3-5 hours after addition, the reaction mixture, which is now a thin suspension, is filtered into a reactor fitted with a mechanical stirrer and nitrogen inlet. This is a clear pale yellow solution, and at this point, the major species present is assumed to be bis-O-(trimethylsilyl(2,R)-((4,S)-(trimethylsiloxycarbonyl)-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioate 23, or possibly its 2-trimethylsiloxy homologue 25. Compound 23 (25) is not isolated as a polytrimethylsilyl species at this stage.

When dipeptide 16 is obtained by crystallization, it is obtained as a highly hydrated solid, with water content>15 wt %. If the water content of 16 is above about 13%, it may be preferable to add extra BSA, in order for the reaction to proceed cleanly to completion. On the other hand, the small amounts of unidentified dehydration products which arise if one dries dipeptide 3 too strongly (see above), can couple with HOBT ester 21, producing impurities which are very similar to acid 1, and which are difficult to remove from the final API. Therefore, counterintuitively, it has been found that this reaction works best with dipeptide 16 which contains 5-15 wt % water, preferably 9-13 wt % water, and that it may help the overall reaction if small amounts of exogenous water are added at the beginning of the reaction. Similarly, acid 7S is most conveniently isolated from its final reaction step via an aqueous precipitation and may be obtained initially containing >10 wt % water. Most of this water can be removed by drying under vacuum at 60° C., and the final coupling step has been found to tolerate 7S which contains up to 5 wt % water without significant effects, although above that the water content may slow down formation of 21. Counterintuitively, it has been found that the final coupling reaction actually gives a cleaner product if both precursor compounds contain optimal amounts of water, and if the acid 7S has below 3% w/w water, it may be advantageous to add small amounts of water to the initial activation step.

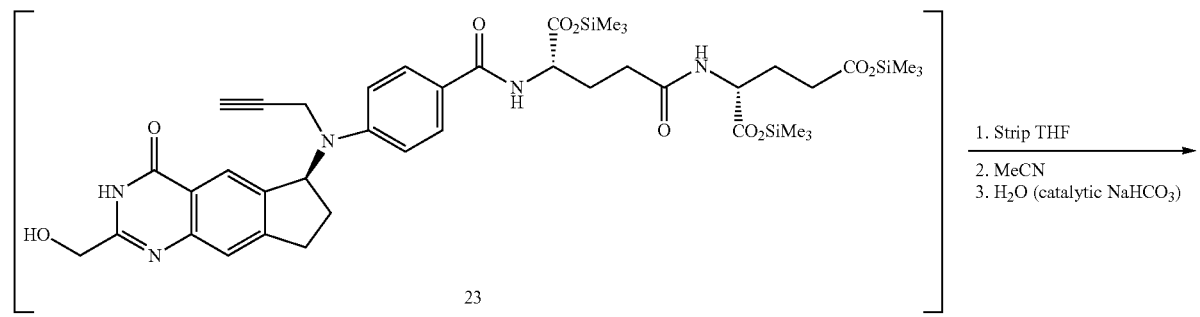

-continued

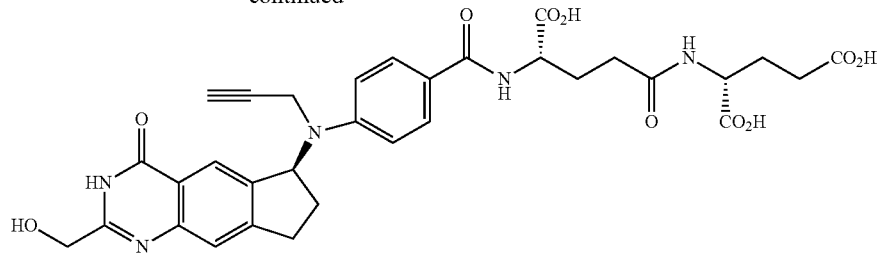

1

As mentioned previously, the major species present in the reaction mixture in this exemplary process of the invention is assumed to be bis-O-(trimethylsilyl (2,R)-((4,S)-(trimethylsiloxycarbonyl)-4-(4,N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioate 23 or higher silylogue 25, although there may be small amounts of lower trimethylsilyl esters also present. These esters may now be hydrolyzed by addition of a relatively small amount of water, aqueous formic acid, or saturated sodium bicarbonate solution.

The silyl esters will hydrolyze spontaneously after water addition and precipitate slowly from the solution. In practice, it has been found that the hydrolysis/precipitation is faster, and gives a more satisfactory solid, if the pH of the added aqueous solution is not near to neutral, and both 2 M formic acid and saturated sodium bicarbonate solution have been used, although saturated sodium bicarbonate solution is preferred. As this precipitation works satisfactorily with 25-100 mol % sodium bicarbonate being added, it can be seen that the main species being precipitated is either the free base (2,R)-((4,S)-carboxy-4-(4,N-MS)-2-(hydroxymethyl)-4-oxo-3,4,7,8-tetrahydro-3H-cyclopenta[g]quinazolin-6-yl)-N-(prop-2-ynyl)amino)benzamido)butanamido) pentanedioic acid 1, or partially the mono-sodium salt. The solution is precipitated at 0 to 5° C. with stirring for several hours, and then the mixture is filtered cold, and the solid is collected on a filter by vacuum filtration under a nitrogen atmosphere, and rinsed with acetonitrile.

When executed properly, this precipitation successfully gets rid of most of the HOBT and excess L-Glu-γ-D-Glu 16 present, as well as most of the byproducts from the BSA, (acetamide, N-trimethylsilylacetamide and hexamethyldisiloxane) and gives a free flowing, though hygroscopic, solid. This purification step may also make the subsequent resin chromatography purification work better. The removal of most of the acetamide at this step may also be useful, as acetamide content of the final API is tightly regulated due to its weak carcinogenicity, and incorporation of this precipitation allows for a lower level of acetamide in the final API.

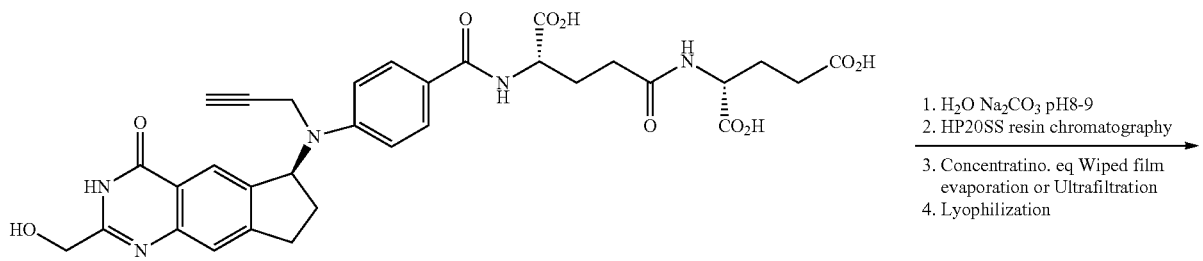

1

1. H₂O Na₂CO₃ pH8-9
2. HP20SS resin chromatography
3. Concentratino. eq Wiped film evaporation or Ultrafiltration
4. Lyophilization

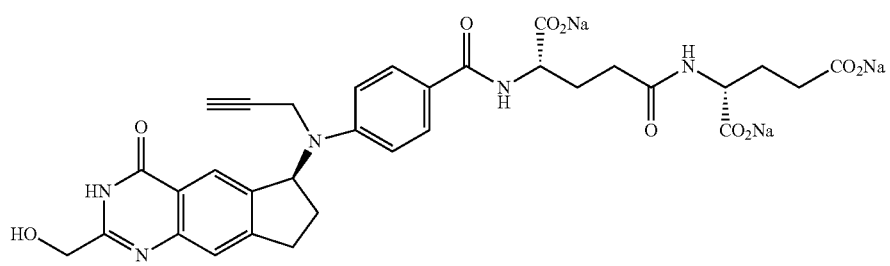

2

BGC945 ONX-0801

The crude solid triacid 1 (or substoichiometric sodium salt thereof) is now dissolved up in cold dilute sodium bicarbonate solution, to give approximately a 25 mg/mL solution of final API, trisodium salt 2. The pH may be adjusted with sodium hydroxide if needed, into the pH 8-9 range, preferably pH 8.5-9.0, and the solution is loaded onto a prewashed and equilibrated (e.g. methanol, then water) chromatography column, such as a HP20SS resin chromatography column, at a nominal ratio of about 50 g resin/1 g of final product. The column is then eluted with many volumes of water only followed by a 1-5% acetonitrile in water gradient if required. Fractions are be monitored by HPLC, and the purer fractions bulked to give a dilute solution of 2 (2-3 g/L) of the desired purity (usually 99.0-99.7 area %).

On a small scale, this material may be lyophilized directly to give the final API 2, in 45-65% overall yield, and >99% purity. Use of more concentrated solutions in the lyophilization leads to shorter and more economical lyophilizations, and the lyophilization cake produced may have better physical properties for subsequent handling and storage. On a larger scale, it may therefore be useful to put in a concentration step prior to the final lyophilization.

The use of a continuous evaporation technique, such as a wiped film evaporator, whereby the API-containing solution is only exposed to moderate heating (~45° C.) for a few seconds per pass through the apparatus, has been shown to concentrate the solution by at least a factor of three per pass through, with no detectable loss of purity or of API.

Alternatively, the API solution can be concentrated by loading it onto resin where it binds more tightly than to HP20SS, and then stripped in much more concentrated form by use of an appropriate solvent. For example, the low concentration solution of API 1, obtained by HP20SS chromatography and pooling of appropriate fractions can be loaded onto an SP207SS resin column, where it adheres. Stripping the column with 25% acetonitrile in water rapidly flushes the API off the column, with at least a 10-fold increase in concentration obtained.

Alternatively, the API solution can be concentrated by use of ultrafiltration. It has been found advantageous to concentrate the column eluant at least fourfold, and possibly as much as sixteenfold by using a chilled 510° C. ultrafiltration apparatus equipped with 5 Pall Centrasette 0.65 Kd cut-off filter membranes. Diafiltration of the retentate in the ultrafiltration apparatus with variable volumes of water (such as an approximately equal volume) has been shown to be advantageous in reducing smaller molecular weight impurities like acetonitrile and acetamide.

An alternative method of hydrolyzing tris-trimethylsilyl ester 23 to the desired API 2 is simply to quench the THF or acetonitrile reaction solution into aqueous sodium carbonate, preferably ensuring that the pH of the final mixture is above 7. This solution can in principle be directly loaded onto a resin column, such as HP20SS, and purified. To reduce material losses, tailing of the API and impurities it may be preferred to prewash the aqueous solution several times with ethyl acetate, prior to the chromatography. HPLC studies show that this removes over half of the HOBT, and considerable amounts of acetamide and THF or acetonitrile prior to the chromatography, but that ONX-0801 does not partition into the ethyl acetate in any appreciable amount. Thus aqueous quenching, and washing with ethyl acetate, offers an alternative to precipitation, and this protocol is considerably more tolerant than the precipitation. Use of repetitive dilution and concentration ultrafiltration cyces on these basic aqueous solutions of 2 will also remove low molecular weight impurities prior to the chromatography leading to further improvements in the overall chromatographic purification. However, better overall results may be obtained with the precipitation, when properly executed.

EXPERIMENTAL SECTION

2R—(N—(S)-4-(Benzyloxycarbonyl)-4-benzyloxycarbonylamino)-1-oxobutyl)amino)pentanedioic acid. 20

To a 250 mL flask (magnetic stirrer, addition funnel and $N_2$ inlet) was charged D-Glutamic acid (10.9 g, 74.1 mmol) and THF (110 mL). Stirring was started as N,O-bis(trimethylsilyl) acetamide (53.1 g, 261 mmol) was added over 5 minutes using the addition funnel. This slurry was stirred for 28 hours at ambient temperature.

To a second 250 mL flask (magnetic stirrer, thermocouple, charging port and $N_2$ inlet) was charged N-benzyloxycarbonyl-L-glutamate-α-benzyl ester (25.0 g, 67.3 mmol) and THF (80 mL) and stirred to obtain a homogeneous solution. The solution was cooled to −25±5° C. and N-methylmorpholine (8.28 g, 81.8 mmol) was added by syringe and the solution stirred at that temperature for about 30 minutes. The 1 L main reaction flask (mechanical stirrer, thermocouple, charging port and $N_2$ inlet) was charged with THF (170 mL) and the THF cooled to −30±5° C. At this point isobutyl chloroformate (10.0 g, 73.2 mmol) was charged and then the N-benzyloxycarbonyl-L-glutamate-α-benzyl ester N-methylmorpholine salt was transferred to the main reaction flask using a piston pump and Teflon tubing at a rate of approximately 2.0 mL/min keeping the temperature of the reaction mixture at −30±5° C. After 45 minutes transfer was complete. The reaction mixture was stirred at −30±5° C. for about 40 minutes (the mixed anhydride/symmetrical anhydride ratio was 95.5/0.28) and then the persilylated D-glutamate ester solution was transferred to the mixed anhydride solution using the pump over 35 minutes keeping the temperature at −30±5° C. during the transfer. The reaction mixture was stirred at this temperature range for 1 hour then slowly allowed to warm to ambient temperature and stirred overnight.

The reaction was carefully quenched by addition of water (75 mL), diluted with EtOAc (200 mL), then acidified to a pH of 1-2 with 37% HCl (1.6 g). The organic phase was washed with water (2×50 mL), 20% brine (2×50 mL) and the organic phase reduced in volume in vacuo to a volume of 112 mL. The product solution was diluted with MeCN (285 mL), transferred to the reaction flask and the solution distilled at atmospheric pressure, collecting 310 mL of distillate. The residue was diluted with 0.2% "water wet" MeCN (456 mL) and heated to reflux to obtain a homogeneous solution. The solution was slowly cooled to ambient temperature and the resulting thick slurry stirred overnight. The solids were collected by filtration, the cake washed with MeCN (45 mL) and the filtrates drawn out under vacuum. The cake was then dried to constant weight under a stream of nitrogen. Yield: 29.2 g (86.8%) Purity: 99.1 A %. C,H,N analysis: Theory; C, 59.99%; H, 5.64%; N, 5.60%. Found: C, 59.96%; H, 5.48%; N, 5.51%

L-Glutamoyl-γ-D-glutamic acid 16

A hydrogenation vessel was charged with 2S—(N—(R)-4-(Benzyloxycarbonyl)-4-benzyloxycarbonylamino)-1-oxobutyl)amino)pentanedioic acid (1.90 kg, 3.796 mol), Pd/C (10%, Degussa type E101-New, 100 g), EtOH (15 L), and water (13.3 L). The resultant mixture was vacuum degassed under nitrogen three times, and stirred under H₂ (40 psi) at ambient temperature for 4 h, and then was checked by LC-MS as well as HPLC. No starting material or partially deprotected intermediate were detected. The hydrogen atmosphere was then removed, and the mixture was purged three times by pressurizing to 40 psi with nitrogen gas, and then releasing the pressure. The reaction mixture was heated to 60° C. and filtered through an 0.2 micron filter, which was then rinsed with further EtOH (10.51 kg) at 60° C. The combined filtrates were stirred at 60° C. until all solids had dissolved up, and 2% thiosilica (40 g) was added and stirring was continued at that temperature for a further 9 hours. The reaction mixture was hot filtered through an 0.2 micron filter, which was rinsed with further hot ethanol (3.8 kg) The combined filtrates were allowed to cool to 22° C. over 12 hours, and were then cooled to 2° C. over a further 12 hours, and the solid was then collected by filtration through GF filter paper and was rinsed with cold (3° C.) ethanol (7.5 kg) and dried in a vacuum oven at 45° C. under a slight nitrogen purge for 20 hours to give L-Glutamoyl-γ-D-glutamic acid 16 (900 g, 85.7%) as a white solid in 99.1 A % purity. Karl Fischer water determination showed 10.9 w/w % water, and Pd analysis showed less than 1 ppm of Pd. $^1$H NMR (D₂O) δ: 1.96-2.02 (1H, m), 2.12-2.23 (3H, m), 2.48 (4H, t, J=7 Hz), 3.82 (1H, t, J=6 Hz), 4.36, 1H, dd, J=8.8, 5 Hz).

(2,R)-((4,S)-carboxy-4-(4,N-(((6S)-2-(hydroxymethyl)-4-oxo-3,4,7,8-tetrahydro-3H-cyclopenta[g] quinazolin-6-yl)-N-(prop-2-ynyl)amino)benzamido) butanamido)pentanedioic acid 1

Acetonitrile (1.5 L) was added to a 5 L three-necked flask equipped with mechanical stirrer, nitrogen inlet and a J-KEM thermometer, stirred at 20±2° C. (6S)-4,N-((2-(hydroxymethyl)-4-oxo-3,4,7,8-tetrahydro-3H-cyclopenta[g] quinazolin-6-yl)-N-(prop-2-ynyl)amino)benzoic acid 7S (50.0 g, 0.1284 mol) and USP-PW water (12.0 g) were added and the mixture was stirred for 30 minutes. N-Hydroxybenzotriazole hydrate (26.2 g, 0.1711 mol) was added, and a temperature drop of ~1° C. was noted. The mixture was stirred vigorously at 20° C. for 2 hours and then N-(3-(N,N-dimethylamino)propyl)-N-ethylcarbodiimide hydrochloride (27.30 g, 0.1419 mol) was added to the slurry and the reaction was allowed to stir at 20±2° C. for 15 hours forming a thick slurry. At this point, an aliquot was removed from the reaction and analyzed by HPLC. The HPLC revealed that the formation of the intermediate hydroxybenzotriazole ester 21 was complete. To the stirred reaction mixture was added L-Glutamyl-γ-D-Glutamic acid (53.20 g, 0.1926 mol), and the reaction mixture was cooled to 2° C., and kept at that temperature for 1 hour, and the reaction mixture was then cooled further to −6° C. Then O,N-bis (trimethylsilyl)acetamide (BSA) (450 mL, 374.4 g, 1.84 mol) was added via an addition funnel over 15 minutes. An exotherm was noted during the addition which was controlled by the rate of BSA addition, the temperature of the reaction rose to 7° C. during the addition. Immediately after the addition, the reaction mixture was stirred on an ice bath for 10 minutes, and then was allowed to warm gradually to 10° C. Two hours and 3.5 hours after completion of the addition aliquots were removed from the reaction and analyzed by HPLC. The HPLC of the 3.5 hour sample revealed that the reaction was complete. After 3.5 hours, the 10° C. suspension was filtered into a 12 L flask equipped with mechanical stirrer and nitrogen inlet. The filter residue was rinsed with further acetonitrile (200 mL), and the contents of the flask were diluted with further acetonitrile (3.5 L). The solution was stirred at 2° C. and then 46 mL of a freshly made up saturated sodium bicarbonate solution (~1.2 M) was added dropwise over 15 minutes causing a light tan precipitate to form. The precipitate was allowed to form for two hours at 2-3° C. and then the mixture was Buchner filtered, washed with acetonitrile (1 L) and dried under suction for 30 minutes, all in a nitrogen atmosphere. A ring of solid had been left in the reaction flask, and this was broken loose and slurried with acetonitrile (500 mL) for 30 minutes. This solid was collected as before by Buchner filtration under nitrogen, rinsed with acetonitrile (100 mL) and dried as was done for the main sample. Both crops were dried at room temperature under high vacuum for fifteen hours, to give 104.1 g and 10.5 g of beige free flowing solid respectively. HPLC analysis showed that both crops were essentially the same material, and they were combined to give 114.6 g (>100%) of crude (2,R)-((4,S)-carboxy-4-(4, N-(((6S)-2-(hydroxymethyl)-4-oxo-3,4,7,8-tetrahydro-3H-cyclopenta[g]quinazolin-6-yl)-N-(prop-2-ynyl)amino)benzamido)butanamido)pentanedioic acid, or a sub-stoichiometric sodium salt thereof, containing less than 1% of the unwanted (2R,4R) diastereoisomer by HPLC analysis.

(2,R)-((4,S)-carboxy-4-(4,N-(((6S)-2-(hydroxymethyl)-4-oxo-3,4,7,8-tetrahydro-3H-cyclopenta[g] quinazolin-6-yl)-N-(prop-2-ynyl)amino)benzamido) butanamido)pentanedioic acid trisodium salt 2

A glass chromatography column was charged with HP-20SS resin (5 kg) slurried in methanol (15 L), and was equilibrated by washing with water (40 L in total). A 12 L three necked flask containing a stirrer and a J-KEM thermometer was charged with freshly made saturated sodium bicarbonate solution (1.1 L) and water (1.1 L), and cooled to 2° C. Crude (2,R)-((4,S)-carboxy-4-(4,N-(((6S)-2-(hydroxymethyl)-4-oxo-3,4,7,8-tetrahydro-3H-cyclopenta[g] quinazolin-6-yl)-N-(prop-2-ynyl)amino)benzamido)butanamido)pentanedioic acid, or a sub-stoichiometric sodium salt thereof, (114.6 g) was added, a slight exotherm of 1° C. was noted, and the solid dissolved up within 10 minutes. After 1 hour the pH was checked, and sodium hydroxide solution (1M, 440 mL) was added slowly to this solution, causing a 2° C. exotherm and raising the pH of the solution to about 7.45. Further sodium hydroxide solution (~10 mL) was added to raise the pH above 8.0 but below 9.0. This solution was charged onto the resin column, and eluted with water (89 L) collecting 20 fractions, but not of equal size. Those fractions (7-18) which HPLC analysis showed to contain the desired material in above 99 A % purity were combined and concentrated from ~56 L to approximately 12 L in an ultrafiltration apparatus using a 5 Pall Centrasette 0.65 Kd cut-off filter membrane, kept at below 10° C. The retentate was diluted with water twice (10, 20 L), and reconcentrated each time to ~12 L. This was then filtered through a Pellicon 2 maxi cassette w/5000 MW cut-off filter, for endotoxin removal, and was placed in a shelf lyophilizer. The product was frozen to −59° C., and was then lyophilized with a shelf temperature of −20° C., with a pressure of 40 mtorr. After 20 hours the shelf temperature was raised to −15° C. for 40 hours, and then to −5° C. for 27 hours. Final drying was done over several days with a shelf temperature of 20° C., and pressures falling to below 10 mtorr, and yielded (2,R)-((4, S)-carboxy-4-(4,N-(((6S)-2-(hydroxymethyl)-4-oxo-3,4,7, 8-tetrahydro-3H-cyclopenta[g]quinazolin-6-yl)-N-(prop-2-ynyl)amino)benzamido)butanamido)pentanedioic acid trisodium salt 2 (44.6 g, 44.35% yield corrected for a KF water analysis of 8.9%) as a fluffy white lyophilizate.

Analytical data. FTIR v: 3283, 1598, 1503, 1397, 1088, 830, 766 cm$^{-1}$. $^1$H NMR (9:1 D$_2$O:CD$_3$OD) δ: 1.63-1.71 (1H, m), 1.82-2.16 (2H, m) 2.22-2.41 (4H, m), 2.42-2.46 (4H, m), 2.72-2.84 (1H, m), 2.87-2.98 (1H, m), 3.56, 3.70 (1H, 1H, ABq, J=18.6 Hz), 3.93 (1H, dd, J=4.8, 8.4 Hz), 4.27 (1H, dd, J=5.0, 7.8 Hz), 4.44 (2H, s), 5.23 (1H, t, J=7.8 Hz), 6.79 (2H, d, J=8.8 Hz), 7.23 (1H, s), 7.53 (2H, d, J=8.8 Hz), 7.61 (1H, s). $^{13}$C NMR (9:1 D$_2$O:CD$_3$OD) δ: 29.49, 29.83, 30.34, 31.26. 33.98, 35.36, 36.95, 56.71, 56.77, 62.02, 64.92, 74.05, 82.60, 114.41, 119.99, 122.28, 122.83, 123.00, 130.01, 142.64, 148.19, 152.07, 153.77, 157.97, 165.34, 170.27, 176.48, 179.84, 180.20, 183.20. Chemical purity (HPLC) 99.8 A %. Diastereoisomeric purity (HPLC) 99.75 A %. CHN: C, 45.41; H, 5.01; N, 8.23, Na 9.85%.

The invention claimed is:

1. A method for the synthesis of a L-Glu-γ-D-Glu dipeptide comprising the steps of:
   a) activating the γ-carboxylic acid of an N-αO-diprotected L-Glu derivative;
   b) silylating D-glutamic acid;
   c) reacting the activated carboxylic acid derivative produced in step a) with the silylated product of step b) to give a protected L-Glu-γ-D-Glu species; and
   d) deprotecting said protected L-Glu-γ-D-Glu species of step c) to produce a L-Glu-γ-D-Glu dipeptide.

2. The method according to claim 1, wherein in step a), activation comprises conversion of the N-αO-diprotected L-Glu derivative into an activated derivative.

3. The method according to claim 2, wherein activation comprises treatment of the N-αO-diprotected L-Glu derivative with an alkyl chloroformate and a tertiary amine base.

4. The method according to claim 3, wherein the chloroformate is isobutyl chloroformate.

5. The method according to claim 2 whereby the N-αO-diprotected L-Glu derivative is added slowly to a low temperature solution of the alkyl chloroformate and tertiary amine base.

6. The method according to claim 5, wherein the solution of the alkyl chloroformate and tertiary amine base is at a temperature of from −10 ° C. to −50 ° C.

7. The method according to claim 3, wherein the tertiary amine base is N-methylmorpholine.

8. The method according to claim 1 wherein the N-αO-diprotected L-Glu derivative is N-benzyloxycarbonyl-L-glutamic acid-α-benzyl ester.

9. The method according to claim 1 wherein in step b), silylation comprises treatment of D-glutamic acid with a silylating agent.

10. The method according to claim 9, wherein the silylating agent is O,N-bis-(trimethylsilyl)acetamide (BSA).

11. The method according to claim 1, wherein in step b), D-glutamic acid is solubilized with several equivalents of a silylating agent; and in step c), that solution is added to a cold solution of the carboxylic acid derivative from step a) to form a silyl esterified solution of a protected L-Glu-γ-D-Glu species.

12. The method according to claim 11 wherein the N-αO-diprotected L-Glu derivative is N-benzyloxycarbonyl-L-glutamic acid-α-benzyl ester and the product is a silyl esterified solution of 2R—(N—(S)-4-(benzyloxycarbonyl)-4-benzyloxycarbonylamino)-1-oxobutyl)amino)pentanedioic acid.

13. The method according to clam 12, wherein, after reaction, the silyl esterified solution of 2R—(N—(S)-4-(benzyloxycarbonyl)-4-benzyloxycarbonylamino)-1-oxobutyl)amino)pentanedioic acid is subjected to a desilylating aqueous work-up, to produce the 2R—(N—(S)-4-(benzyloxycarbonyl)-4-benzyloxycarbonylamino)    -1-oxobutyl)amino)pentanedioic acid.

14. The method according to claim 13, wherein the de-silylating work-up comprises partition of the solution between water and an organic solvent.

15. The method according to claim 1, wherein deprotection comprises removal of benzyl and/or benzyloxycarbonyl protecting groups to produce L-Glutamyl-γ-D-Glutamic acid.

16. The method according to claim 1, wherein deprotection comprises hydrogenolysis.

17. method according to claim 16, wherein hydrogenolysis comprises hydrogenolysis in aqueous ethanol, with an appropriate transition metal catalyst.

18. The method according to claim 17, wherein the catalyst comprises a palladium on carbon catalyst.

19. The method according to claim 1 wherein the deprotected product is treated with thiosilica gel, to obtain a product containing <10 ppm of palladium.

20. A compound selected from:
   (R)-bis(O-trimethylsilyl) 2-((S)-5-(benzyloxy)-4-(benzyloxycarbonylamino)-5-oxopentanamido)pentanedioate;
   (R)-2-((S)-5-(benzyloxy)-4-(benzyloxycarbonylamino)-5-oxopentanamido)pentanedioic acid;
   (S)-O-1H-benzo[d][1,2,3]triazol-1-yl 4-((2-(hydroxymethyl)-4-oxo-4,6,7,8-tetrahydro-3H-cyclopenta[g]quinazolin-6-yl)-N-(prop-2-ynyl)amino)benzoate;
   (R)-bis(O-trimethylsilyl) 2-((S)-4-(4-(((S)-2-(hydroxymethyl)-4-oxo-4,6,7,8-tetrahydro-3H-cyclopenta[g]quinazolin-6-yl)-N-(prop-2-ynyl)amino)benzamido)-5-oxo-5-(trimethylsilyloxy)pentanamido)pentanedioate;
   (S)-O-1H-benzo[d][1,2,3]triazol-1-yl 4-((2-(trimethylsiloxymethyl)-4-oxo-4,6,7,8-tetrahydro-3H-cyclopenta[g]quinazolin-6-yl)-N-(prop-2-ynyl)amino)benzoate;
   (R)-bis(O-trimethylsilyl) 2-((S)-4-(4-(((S)-2-(trimethylsiloxymethyl)-4-oxo-4,6,7,8-tetrahydro-3H-cyclopenta[g]quinazolin-6-yl)-N-(prop-2-ynyl)amino)benzamido)-5-oxo-5-(trimethylsilyloxy)pentanamido)pentanedioate.

* * * * *